(12) United States Patent
Reich et al.

(10) Patent No.: US 11,921,181 B2
(45) Date of Patent: Mar. 5, 2024

(54) **HIGH-RESOLUTION CEREBROSPINAL FLUID-SUPPRESSED T2*-WEIGHTED MAGNETIC RESONANCE IMAGING OF CORTICAL LESIONS**

(71) Applicants: Daniel Salo Reich, Bethesda, MD (US); Erin Savner Beck, Bethesda, MD (US); Govind Nair, Bethesda, MD (US); Neville Dali Gai, Bethesda, MD (US)

(72) Inventors: Daniel Salo Reich, Bethesda, MD (US); Erin Savner Beck, Bethesda, MD (US); Govind Nair, Bethesda, MD (US); Neville Dali Gai, Bethesda, MD (US)

(73) Assignee: THE UNITED STATES OF AMERICA, AS REPRESENTED BY THE SECRETARY, DEPARTMENT OF HEALTH AND HUMAN SERVICES, Bethesda, MD (US)

( * ) Notice: Subject to any disclaimer, the term of this patent is extended or adjusted under 35 U.S.C. 154(b) by 139 days.

(21) Appl. No.: 17/593,365

(22) PCT Filed: Apr. 24, 2020

(86) PCT No.: PCT/US2020/029823
§ 371 (c)(1),
(2) Date: Sep. 16, 2021

(87) PCT Pub. No.: WO2020/219886
PCT Pub. Date: Oct. 29, 2020

(65) Prior Publication Data
US 2022/0268867 A1    Aug. 25, 2022

Related U.S. Application Data

(60) Provisional application No. 62/838,578, filed on Apr. 25, 2019.

(51) Int. Cl.
  *G01V 3/00* (2006.01)
  *A61B 5/00* (2006.01)
  (Continued)

(52) U.S. Cl.
  CPC ........ *G01R 33/5607* (2013.01); *A61B 5/0042* (2013.01); *A61B 5/055* (2013.01);
  (Continued)

(58) Field of Classification Search
  CPC .............. G01R 33/3415; G01R 33/543; G01R 33/5659; G01R 33/36; A61B 5/055; A61B 324/309
  (Continued)

(56) References Cited

U.S. PATENT DOCUMENTS

| 8,452,065 B2 * | 5/2013 | Azar | A61B 5/055 382/131 |
| 2010/0232667 A1 * | 9/2010 | Azar | A61B 5/418 600/420 |

(Continued)

FOREIGN PATENT DOCUMENTS

CN       102362192 A  *  2/2012  ......... G01R 33/5611

OTHER PUBLICATIONS

Rydberg, J. et al., "Contrast Optimization of Fluid-Attenuated Inversion Recovery (FLAIR) Imaging," Magnetic Resonance in Medicine, vol. 34, No. 6, Dec. 1995, 10 pages.
(Continued)

*Primary Examiner* — Walter L Lindsay, Jr.
*Assistant Examiner* — Frederick Wenderoth
(74) *Attorney, Agent, or Firm* — McCoy Russell LLP

(57) ABSTRACT

Provided herein are methods and systems for high-resolution, cerebrospinal fluid-suppressed T2*-weighted magnetic resonance imaging of cortical lesions.

36 Claims, 11 Drawing Sheets

(51) Int. Cl.
| | |
|---|---|
| A61B 5/055 | (2006.01) |
| G01R 33/56 | (2006.01) |
| G01R 33/563 | (2006.01) |
| G01R 33/565 | (2006.01) |

(52) U.S. Cl.
CPC ..... *G01R 33/5602* (2013.01); *G01R 33/5608* (2013.01); *G01R 33/56341* (2013.01); *G01R 33/56509* (2013.01)

(58) Field of Classification Search
USPC .......................................................... 324/309
See application file for complete search history.

(56) References Cited

U.S. PATENT DOCUMENTS

| | | | | |
|---|---|---|---|---|
| 2015/0309146 | A1* | 10/2015 | Jin | A61B 5/055 324/309 |
| 2015/0310640 | A1* | 10/2015 | Hardy | G06T 7/0012 382/131 |
| 2016/0220168 | A1* | 8/2016 | Port | A61B 5/0042 |

OTHER PUBLICATIONS

Gutteridge, S. et al., "Mapping the Absolute Value of M0 Using Dipolar Field Effects," Magnetic Resonance in Medicine, vol. 47, No. 5, May 2002, 9 pages.

Stanisz, G. et al., "T1, T2 Relaxation and Magnetization Transfer in Tissue at 3T," Magnetic Resonance in Medicine, vol. 54, No. 3, Sep. 2005, 6 pages.

Sehgal, V. et al., "Clinical Applications of Neuroimaging With Susceptibility-Weighted Imaging," Journal of Magnetic Resonance Imaging, vol. 22, No. 4, Oct. 2005, 12 pages.

Haacke, E. et al., "Characterizing Iron Deposition in Multiple Sclerosis Lesions Using Susceptibility Weighted Imaging," Journal of Magnetic Resonance Imaging, vol. 29, No. 3, Mar. 2009, 8 pages.

Shin, W. et al., "Fast High-Resolution T1 Mapping using Inversion-Recovery Look-Locker Echo-Planar Imaging at Steady State: Optimization for Accuracy and Reliability," Magnetic Resonance in Medicine, vol. 61, No. 4, Apr. 2009, 21 pages.

Gai, N. et al., "Modulated Repetition Time Look-Locker (MortlI): A Method for Rapid High Resolution Three-Dimensional T1 Mapping," Journal of Magnetic Resonance Imaging, vol. 30, No. 3, Sep. 2009, 23 pages.

Zwanenburg, J. et al., "Fast high resolution whole brain T2* weighted imaging using echo planar imaging at 7 T," NeuroImage, vol. 56, No. 4, Jun. 15, 2011, Available Online Mar. 31, 2011, 6 pages.

De Graaf, W. et al., "Lesion detection at seven Tesla in multiple sclerosis using magnetisation prepared 3D-FLAIR and 3D-DIR," European Radiology, vol. 22, No. 1, Aug. 27, 2011, 11 pages.

Wu, B. et al., "Fast and Tissue-Optimized Mapping of Magnetic Susceptibility and T2* with Multi-Echo and Multi-Shot Spirals, " Neuroimage, vol. 59, No. 1, Jan. 2, 2012, 21 pages.

Zhang, Y. et al., "Quantitative Susceptibility Mapping and R2* Measured changes during White Matter Lesion Development in Multiple Sclerosis: Myelin Breakdown, Myelin Debris Degradation and Removal, and Iron Accumulation," American Journal of Neuroradiology, vol. 37, No. 9, Sep. 2016, 7 pages.

Sati, P. et al., "The central vein sign and its clinical evaluation for the diagnosis of multiple sclerosis: a consensus statement from the North American Imaging in Multiple Sclerosis Cooperative," Nature Reviews. Neurology, vol. 12, No. 12, Dec. 2016, Available Online Nov. 11, 2016, 9 pages.

Bojorquez, J. et al., "What are normal relaxation times of tissues at 3 T?," Magnetic Resonance Imaging, vol. 35, Jan. 2017, 12 pages.

ISA European Patent Office, Written Opinion of the International Searching Authority Issued in Application No. PCT/US2020/029823, dated Sep. 9, 2020, WIPO, 8 pages.

ISA European Patent Office, International Search Report Issued in Application No. PCT/US2020/029823, dated Sep. 9, 2020, WIPO, 3 pages.

Beck, E. et al., "Inversion Recovery Susceptibility Weighted Imaging With Enhanced T2 Weighting at 3 T Improves Visualization of Subpial Cortical Multiple Sclerosis Lesions," Investigative Radiology, vol. 55, No. 11, Nov. 2020, 9 pages.

* cited by examiner

HIGH-RESOLUTION CEREBROSPINAL FLUID-SUPPRESSED T2*-WEIGHTED MAGNETIC RESONANCE IMAGING OF CORTICAL LESIONS

CROSS REFERENCE TO RELATED APPLICATIONS

The present application is a U.S. National Stage of PCT Patent Application No. PCT/US2020/029823, entitled "High-Resolution Cerebrospinal Fluid-Suppressed T2*-Weighted Magnetic Resonance Imaging of Cortical Lesions" and filed on Apr. 24, 2020. Application No. PCT/US2020/029823 claims priority to U.S. Provisional Application No. 62/838,578, entitled "High-Resolution Cerebrospinal Fluid-Suppressed T2*-Weighted Magnetic Resonance Imaging of Cortical Lesions" and filed on Apr. 25, 2019. The entire contents of the above-listed applications are hereby incorporated by reference in their entirety for all purposes.

FIELD OF THE INVENTION

The present invention relates to methods and systems for high-resolution, cerebrospinal fluid-suppressed T2*-weighted magnetic resonance imaging (MRI) of cortical lesions.

BACKGROUND OF THE INVENTION

Cortical lesions are common in neurologic disease, including multiple sclerosis (MS). Pathological changes in the cerebral cortex in MS include demyelination, neuronal loss, gliosis, and loss of intracellular iron. There is evidence that the pathophysiology of these lesions differs from that of lesions in white matter. Cortical lesions, and especially subpial cortical lesions that touch the pial surface of the brain, may form independently from white matter lesions, perhaps due to leptomeningeal inflammation. In addition, cortical lesions may contribute independently to disability. MRI is an essential tool for clinical management of and research on MS and other neurological conditions, including diagnosis, prognosis, response to treatment, and outcome measures in clinical trials, as well as for providing insights into the underlying pathophysiology.

While cortical lesions are known from histopathology studies to be common in MS, they have so far been difficult to visualize on MRI, especially at clinically accessible magnetic field strength. Cortical lesions are difficult to detect in routine imaging due to the small dynamic range in signal changes induced by the lesions in comparison to the overall dynamic range. In addition, the close proximity of the cortical lesion, especially of the superficial or "subpial" type of lesion, to cerebrospinal fluid (CSF), can greatly obscure its visualization if the signal intensities from the two tissue types are similar. MRI at standard clinical magnetic field strength is almost completely insensitive.

At higher field (7 tesla, 7 T), cortical lesions have been detected using T2*-weighted images and T1 mapping sequences. The visibility is much reduced at lower fields (which are commonly available for clinical use, such as 3 T), because of the changes to relaxation properties as well as lower signal to noise ratio (SNR) at lower field strengths. Currently available approaches that have been designed to detect cortical lesions at 3 T—including double inversion recovery (DIR) and phase-sensitive inversion recovery (PSIR) imaging—are more sensitive to these signal changes than more standard MRI techniques, but are still poorly sensitive to many cortical lesions, especially subpial lesions, which are thought to underlie substantial clinical disability.

DIR, a sequence with suppressed cerebrospinal fluid (CSF) and white matter signal, is limited by low signal and artifacts, leading to low sensitivity for cortical lesions and high false positive rates. When compared to postmortem pathology, 3 T DIR was 83% sensitive for leukocortical lesions, but only 7% sensitive for subpial lesions. PSIR has also been used for cortical lesion visualization at 3 T. While PSIR appears to improve sensitivity to leukocortical lesions, data on improvement in subpial lesion detection has been inconsistent. More recently, T1-weighted magnetization-prepared 2 rapid acquisition gradient echoes (MP2RAGE) and its derived images such as bias-free T1-weighted images and T1-maps, have been used for cortical lesion detection at 3 T, with a similar cortical lesion detection rate as DIR, and at 7 T.

T2*-weighted methods at 7 T have also been used to image cortical lesions, with substantial improvement in subpial lesion detection rate in MS compared to 3 T. The increased sensitivity of T2* weighting for cortical demyelination at ultra-high field is likely due to a combination of increased sensitivity to loss of myelin as well as to loss of iron. In addition, ultra-high field strength makes it easier to obtain higher resolution scans due to the increased signal-to-noise ratio (2-fold increase in signal-to-noise ratio at 7 T compared to 3 T), enabling detection of smaller lesions. Nevertheless, 3 T clinical scanners could potentially be made more sensitive to subpial lesions by increasing the lesion contrast relative to surrounding tissue such as CSF and cortical gray matter through CSF-nulling and optimal parameter selection.

Accordingly, there is a need for better visualization of cortical lesions in order to understand their dynamics, their clinical importance, and their response to MS treatment. More accurate methods for visualizing cortical lesions are key to better understanding their clinical implications and their response to MS therapies. Improved visualization may also be relevant to disease differential diagnosis, prognostication, and detection of response to therapy.

SUMMARY OF THE INVENTION

Provided herein is a method of visualizing a cortical lesion in a subject using an MRI system. The MRI system may perform a MRI sequence described herein at a field strength of 1.5, 3, or 7 tesla (T), which in some examples may be 1.5 or 3 T. The method may comprise acquiring signal data with the MRI system by performing a T2*-weighted sequence that suppresses cerebrospinal fluid (CSF) signals. From the signal data, one or more high resolution images may be produced, which may be at a computer system of the MRI system. The high resolution images may be indicative of (demonstrate) the presence of cortical lesions. The T2*-weighted sequence may be sensitized with a diffusion gradient, and the MRI system may thereby produce diffusion-weighted images at a high isotropic resolution of about 0.6 mm or finer, and 0.6 mm in one example. The diffusion gradient may suppress CSF signals, and the b-value of the diffusion gradient may be 500-1200 s/mm$^2$ or higher, and 500-1200 s/mm$^2$ in one example. The T2*-weighted sequence may be repeated, and the signal data acquired from the sequences averaged to produce the one or more high resolution images. The signal data acquired from the T2*-weighted sequence may be motion corrected before producing the one or more high resolution images.

The T2*-weighted sequence may comprise a 3D-T2*-weighted multi-shot acquisition sequence, and may further comprise a T2-prepared inversion pulse (T2Prep) followed by an inversion pulse. The T2Prep may suppress CSF signals, and the inversion time of the inversion pulse may be tuned to the null point of CSF. The T2Prep may comprise a $90_x$-$180_y(4)$-$90_x$ pulse, and the duration of the T2-Prep pulse may be based on the calculated time at which gray matter (GM) and white matter (WM) signals are equal based on their initial magnetization values. The signal data acquired from the T2*-weighted sequence may be motion corrected before producing the one or more high resolution images. The one or more high resolution images may be processed from magnitude and phase images produced by the T2*-weighted sequence. The T2*-weighted sequence may comprise performing vascular crushing before the acquisition, which may suppress vascular signals. An echo train may be acquired in a centric fashion.

The method may further comprise performing one or more of a T1-weighted magnetization-prepared 2 rapid acquisition gradient echoes (MP2RAGE) sequence and a fluid-attenuated inversion recovery (FLAIR) sequence. The signal data produced by one or more of MP2RAGE and FLAIR may be used to produce one or more images. The one or more images produced by the T2*-weighted and one or more of MP2RAGE and FLAIR sequences may be indicative of the presence of the cortical lesion. The images produced by the T2*-weighted sequence may be compared to the images produced by the MP2RAGE or FLAIR sequences, or the combination thereof. The comparison may be used to demonstrate the presence or absence of the cortical lesion.

The T2*-weighted sequence may be repeated 2-4 times, and the signal data acquired from the sequences averaged to produce the one or more high resolution images. In one example, the T2*-weighted sequence may be performed twice. The average may be a voxel-wise median.

Further provided herein is an MRI system comprising an MRI device and a computer system. The MRI device may comprise a magnet system to apply a polarizing magnetic field about at least a portion of a subject arranged in the MRI system; a plurality of gradient coils to apply a gradient field to the polarizing magnetic field; and, a radiofrequency (RF) system to apply a RF excitation field to a region of interest in the subject and acquire signal data therefrom. The polarizing magnetic field may be 1.5, 3, or 7 tesla. The computer system may have a processor and a memory. The computer system may perform a T2*-weighted sequence by controlling the MRI device, wherein the sequence suppresses CSF signals; acquire high resolution signal data generated by the sequence; and, produce one or more high resolution images from the signal data. The computer system may control the MRI device to sensitize the T2*-weighted sequence with a diffusion gradient; and, produce diffusion-weighted images at a high isotropic resolution of about 0.6 mm or finer, which may be 0.6 mm. The diffusion gradient may suppress CSF signals, and the b-value of the diffusion gradient may be 500-1200 s/mm² or higher, which may be 500-1200 s/mm². The computer system may control the MRI device to repeat the T2*-weighted sequence; and, may average the signal data acquired from the T2*-weighted sequences to produce the one or more high resolution images. The average may be a voxel-wise median. The computer system may motion correct the signal data acquired from the T2*-weighted sequence before producing the one or more high resolution images.

The T2*-weighted system may comprise a 3D-T2*-weighted multi-shot acquisition sequence, and further comprise a T2-prepared inversion pulse (T2Prep) followed by an inversion pulse, wherein the T2Prep suppresses CSF signals. The T2Prep may comprise a $90_x$-$180_y(4)$-$90_x$ pulse, and the duration of the T2-Prep pulse may be based on the calculated time at which GM and WM signals are equal based on their initial magnetization values. The computer system may tune the inversion time of the inversion pulse produced by the MRI device to the null point of CSF. The computer system may control the MRI device to repeat the T2*-weighted sequence 2-4 times, particularly twice; and, average the signal data acquired from the T2*-weighted sequences to produce the one or more high resolution images. The average may be a voxel-wise median. The computer system may motion correct the signal data acquired from the T2*-weighted sequence before producing the one or more high resolution images. The computer system may process magnitude and phase images produced by the T2*-weighted sequence to generate the one or more high resolution images.

The computer system may control the MRI device to perform vascular crushing before the acquisition to suppress vascular signals. The computer system may acquire an echo train in a centric fashion. The computer system may also control the MRI device to further perform one or more of a MP2RAGE and a FLAIR sequence, acquire MP2RAGE signal data and FLAIR signal data from these one or more sequences to produce one or more MP2RAGE high-resolution images, FLAIR high-resolution images, or a combination thereof. The one or more high-resolution images from the one or more T2*-weighted sequences may be compared to the high-resolution images from the one or more MP2RAGE and FLAIR sequences. The comparison may be indicative of a cortical lesion. In one example, the T2*-weighted sequence is performed twice in combination with the MP2RAGE and FLAIR sequences.

BRIEF DESCRIPTION OF THE DRAWINGS

FIG. 2A. Mz evolution for IR-SWIET at steady-state. Arrows indicate beginning and end of each epoch. Black arrows indicate beginning and end of data acquisition. GM=gray matter, WM=white matter, CSF=cerebrospinal fluid. FIG. 2B. Schematic diagram for the IR-SWIET sequence. Arrows shown correspond to the magnetization epoch portrayed in (FIG. 2A).

FIG. 5A: single acquisition. FIG. 5B: median of two acquisitions. FIG. 5C: median of four acquisitions. Arrows denote cortical lesions.

images. IR-SWIET is a 3D sequence acquired with isotropic voxels, allowing for reconstruction in axial (FIG. 6A), coronal (FIG. 6B), and sagittal (FIG. 6C) planes. IR-SWIET images have suppressed CSF signal, making cortical lesions easier to see. (FIGS. 6A-C) White matter lesions (light arrows) and cortical lesions (dark arrows) are conspicuous and central veins (asterisk) can be seen in some lesions. Lesions in the brainstem (FIG. 6D, light arrowhead) and cerebellum (FIG. 6E, light arrowhead) are also observed. All images are the median of four IR-SWIET acquisitions.

FIG. 7A) Subpial lesions (dark arrow) are well seen on IR-SWIET images compared to other 3 T images and are confirmed as lesions on 7 T images. FIG. 7B) High magnification view of 2 subpial lesions identified on IR-SWIET but which are more subtle or not seen on other 3 T images and are confirmed on 7 T images. IR-SWIET—inversion recovery susceptibility weighted imaging with enhanced T2 weighting (×2—average of 2 acquisitions, ×4—average of 4 acquisitions), DIR—double inversion recovery, MP2RAGE—magnetization-prepared rapid gradient echo, SWI—susceptibility weighted imaging, FLAIR—fluid-attenuated inversion recovery, PSIR—phase sensitive inversion recovery, GRE—gradient recalled echo.

FIG. 9A) Percent of 7 T subpial lesion volume detected was higher for IR-SWIET×4 than for other 3 T sequences. FIG. 9B) The average volumes of detected and undetected subpial lesions were similar between 3 T sequences. *=p<0.05, , p<0.01, *=p<0.001, ***=p<0.0001, IR-SWIET—inversion recovery susceptibility weighted imaging with enhanced T2 weighting (×2—average of 2 acquisitions, ×4—average of 4 acquisitions), DIR—double inversion recovery, MP2RAGE—magnetization-prepared rapid gradient echo, SWI—susceptibility weighted imaging, FLAIR—fluid-attenuated inversion recovery, PSIR—phase-sensitive inversion recovery.

FIG. 11A) Subpial lesion classification is more accurate on IR-SWIET than on MP2RAGE, FLAIR, and DIR, and IRSWIET/MP2RAGE/FLAIR is more accurate than DIR/M2RAGE/FLAIR. *=p<0.05, **=p<0.01. FIG. 11B) Correlation between subpial lesions identified on 3 T vs 7 T is higher for IR-SWIET×4, IRSWIET/MP2RAGE/FLAIR, and DIR/MP2RAGE/FLAIR than for MP2RAGE, DIR, or PSIR. IR-SWIET—inversion recovery susceptibility weighted imaging with enhanced T2 weighting (×2—average of 2 acquisitions, ×4—average of 4 acquisitions), DIR—double inversion recovery, MP2RAGE—magnetization-prepared rapid gradient echo, SWI—susceptibility weighted imaging, FLAIR—fluid-attenuated inversion recovery, PSIR—phase-sensitive inversion recovery.

DETAILED DESCRIPTION

Figure 1:
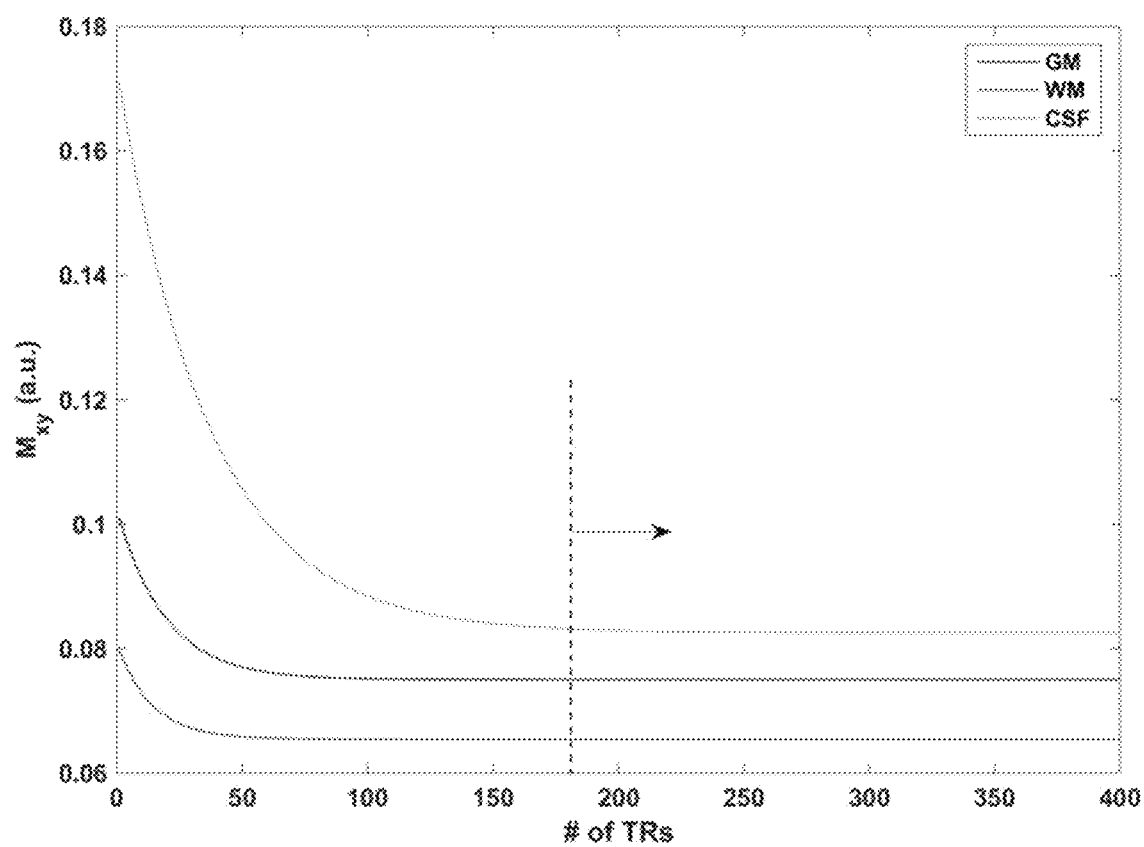
FIG. 1 shows transverse magnetization for SWI. The arrow indicates beginning of acquisition in steady-state.

The inventors have discovered that T2*-weighted imaging at high-resolution, together with suppression of the CSF signal, is superior to other known methods for detecting cortical lesions, especially subpial lesions. The technique takes advantage of the T2* signal increase that is in part induced by reduced iron concentration in cortical lesions, and is deployed at high-resolution to allow visualization of small lesions and thin lesions that lay on the subpial surface of the brain.

Two distinct approaches have been tested by the inventors and are detailed herein. CSF suppression was achieved in high-resolution T2*-weighted sequences in the first approach through application of a diffusion gradient (DWI approach), and in the second, by selecting an inversion time (TI) corresponding to the null point of CSF (IR-SWIET approach).

Diffusion-weighted brain MR imaging is used in standard clinical brain imaging at various clinical and non-clinical field strengths (including 1.5 and 3 T), mainly for detection of acute strokes and areas of active tissue destruction, as well as certain tumors. The inventors realized that commonly used diffusion imaging techniques employ the echo-planar imaging (EPI) sequence, which is uniquely sensitive to T2* and susceptibility changes in tissue. The inventors further recognized that images acquired at moderate-to-high b-value suppress the CSF signal, enabling sensitive imaging of T2* and susceptibility changes in tissue. In addition, diffusion tensor images are acutely sensitive to microstructural changes in tissue. This makes high-resolution diffusion images ideally suited for imaging iron loss and microstructural changes that occur in these lesions. Indeed, in imaging patients with MS, the inventors noticed that areas of subtle signal abnormality are frequently seen on diffusion-weighted images in the cortex of MS patients, which are substantially better seen on these images than on other scans obtained as part of the clinical routine. Similar lesions have not been observed in healthy volunteers or in patients with other neuro-inflammatory and neuro-infectious diseases, who are frequently imaged under similar clinical protocols.

Specifically, the first approach—the DWI approach—may use large diffusion gradients to suppress CSF, EPI acquisition at a relatively short echo time (TE) of 70-100 ms for better SNR, and a scheme to acquire images at high resolution of about 0.6 mm per voxel edge. The inventors optimized the pulse sequence parameters to achieve high resolution while also optimizing lesion visualization. To achieve reliable visualization (good SNR), despite higher resolution and longer sampling time required to achieve it, a relatively lower TE of ~80 ms may be used. Monopolar diffusion gradients and a moderate b-value of 500-1200 s/mm$^2$ may be used to achieve this. The modifications may be accomplished utilizing the options already available on a Siemens 3 T scanner, or other scanners commonly used in the art. The images may be acquired with 3 orthogonal or 6 or more non-colinear directions of the diffusion gradient, and the non-zero b-value images may be averaged for visualizing the DWI trace. Further improvements in SNR can be achieved by signal averaging the acquisition in each diffusion direction 2-4 times. The resulting diffusion-weighted trace image also has T2* weighting from the EPI acquisition, which is essential for visualization of cortical lesions. Trace-DWI can be produced on the scanner and used directly. It may also be useful to remove any motion that occurred during acquisition, and motion correction using registration can be done prior to averaging off-line for better results.

The second approach is to suppress CSF in an optimal high-resolution 3D-T2*-weighted image using inversion recovery susceptibility weighted imaging (SWI) with enhanced T2-weighting (IR-SWIET). While SWI images can be generated from the magnitude and phase images acquired using the IR-SWIET technique, the inventors have discovered that the magnitude images are sufficient for visualization of cortical lesions. Some cortical lesions are visible on routine high-resolution multishot 3D-T2*-weighted images, but a majority of them are difficult to identify due to the high signal from CSF. The T2-prepared inversion recovery multishot acquisition along with appropriate contrast enhancement mechanism employed in an IR-SWIET sequence reduces many of the false-positive hyperintensities seen in high-resolution diffusion-weighted images. In addition, modification to suppress artifactual hyperintense vessel signal has been implemented. The images produced on an MRI scanner can be used directly for visualization. The sequence can be repeated 2-4 times and averaged for increased SNR. Motion correction may be used before averaging and visualization to improve the image quality.

The inventors have determined that, for both the DWI and IR-SWIET approaches, phased-array coils greatly improve visualization of the abnormal MRI signal in cortical lesions due to improved signal-to-noise ratio in superficial brain structures. In particular, the two approaches provide dramatic improvements over standard T2-FLAIR, T2, and T1-weighted sequences, as well as modifications thereof that are in general clinical use for visualizing cortical lesions.

1. MRI-Based Methods for Detecting Cortical Lesions

Provided herein is an MRI method for detecting cortical lesions, which may be subpial. The method may be performed on a subject, which may be an animal, and which may further be a mammal such as a primate or ape, or more specifically a human. The subject may have or may be suspected to have MS, epilepsy, or suffered from a stroke, or he/she may have another disease process that affects the cerebral cortex, such as dysplasia or neurodegeneration. In one example, the subject may have or be suspected to have MS.

In particular, provided herein is a method of producing an image indicative of the cortical lesion using an MRI system. The method may comprise acquiring data with the MRI system by performing a high resolution T2*-weighted sequence that suppresses CSF signals. The T2* weighting may be used to detect T2* signal increases induced by reduced iron concentrations, as well as microstructural changes, in cortical lesions.

a. DWI

In one embodiment, the method may comprise diffusion-weighted imaging (DWI), which may be performed at a magnetic field strength of 1.5 or 3 tesla (T). The DWI may comprise at least one EPI sequence. The DWI sequence may comprise large diffusion gradients to sensitize diffusing spins. The EPI acquisition may be performed at an echo time (TE) of 70-100 ms, which may be used to acquire images at a near-isotropic resolution of about 0.6 mm per voxel edge.

The DWI sequence may also comprise monopolar diffusion gradients, and comprise moderate b-values, in order to suppress CSF signals (typically ranging between 500-1200 $s/mm^2$). Images may be acquired with 3 orthogonal or 6 or more non-colinear directions of the diffusion gradient. Non-zero b-value images may be averaged to visualize the DWI trace. The method may comprise acquiring repetitions of the sequence (typically 2-4 repetitions). The individual acquisitions may be averaged to increase the SNR. Trace-DWI may be produced on the MRI scanner and may be used directly to visualize cortical lesions. Motion that occurred during acquisition may be mitigated using registration prior to averaging, which may be performed off-line.

The DWI sequence may comprise simultaneous multi-slice imaging or highly parallel imaging. In one embodiment, the DWI sequence may comprise the sequence shown in FIG. 3. In such a sequence, the depicted gradients may be monopolar diffusion gradients as described above. In another embodiment, the DWI sequence may comprise the following parameters:

| | |
|---|---|
| TR/TE | 21.8 s/73 ms |
| b value | 800 $s/mm^2$ |
| Diffusion directions | 6 non-colinear directions |
| FOV | 195 mm × 195 mm |
| Acquisition matrix | 312 × 312 |
| In-plane resolution | 0.62 mm × 0.62 mm |
| Slice thickness | 0.6 mm |
| Acquisition time | 11 min 17 sec |

The MRI system used to implement the method may comprise phased-array coils.

b. IR-SWIET

In another embodiment, the T2*-weighted sequence may comprise optimal high-resolution 3D-T2*-weighted imaging, which may comprise inversion recovery susceptibility weighting combined with enhanced T2 weighting (referred to as IR-SWIET). The method may comprise an inversion recovery (IR) multishot acquisition with an inversion time (TI) tuned to the null point of CSF, and T2-preparation to enhance T2 contrast in the images.

The IR-SWIET sequence may maintain T2* contrast similar to a 3D SWI sequence known in the art, and introduce T2 contrast at null point of CSF using T2-preparation. SWI images may be generated from the magnitude and phase images acquired using the IR-SWIET pulse sequence, but the magnitude images may be sufficient for visualization of cortical lesions. The parameters for the IR-SWIET may also correspond to 3D SWI, as known in the art. In particular, the parameters may comprise the following:

| | |
|---|---|
| TR/TE (ms) | 58/32 |
| TI (ms) | 2650 |
| TFE factor | 22 |
| EPI factor | 23 |
| Flip angle | 10° |
| Shot duration | 10000 |
| SENSE (y/z) | 2.5/2 |
| Resolution (mm³) | 0.8 × 0.86 × 0.64 (reconstructed at 0.64 × 0.64 × 0.64) |
| Scan time | 5:08 |

Figure 2A:
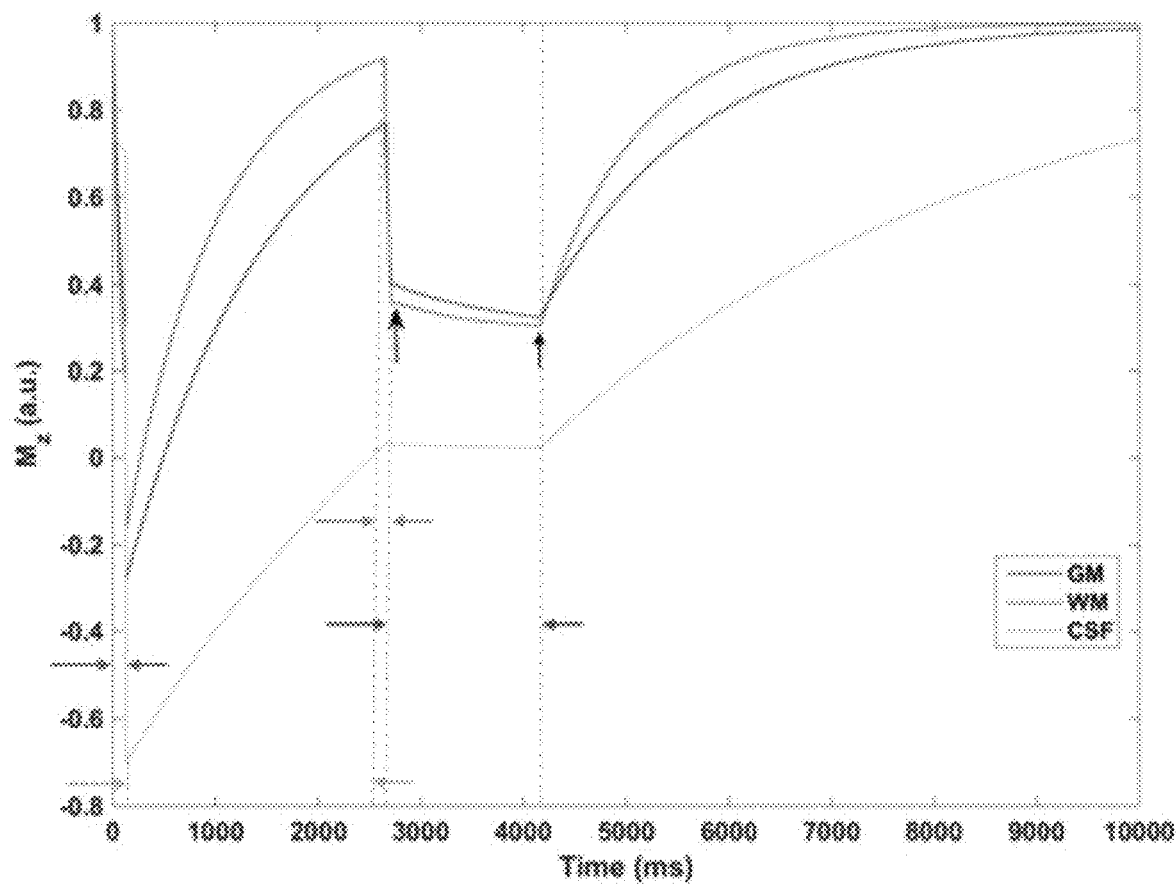
FIGS. 2A-B show development of the inversion recovery susceptibility weighted imaging with enhanced T2 weighting (IR-SWIET) sequence.
Figure 2B:
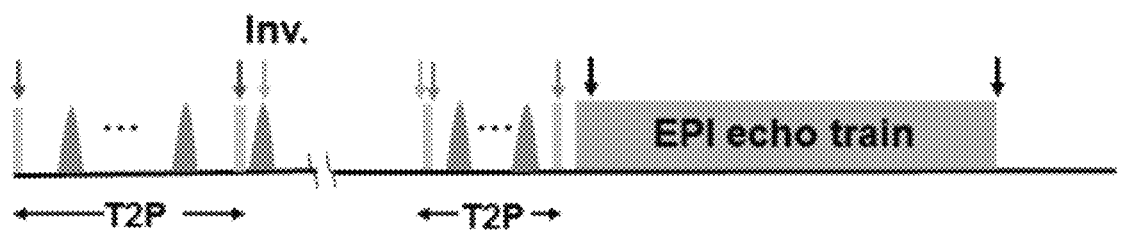

The IR-SWIET sequence is as shown in FIG. 2. The IR-SWIET-generated images may be acquired at steady-state, which may be as indicated in FIG. 1 (arrow). In one embodiment, the echo train may be acquired centrically. A SWI sequence known in the art or as described herein may be modified to suppress CSF using $90_x$-$180_y$(4)-$90_x$ T2Prep followed by inversion and acquisition at CSF-null point, which may be similar to known preparation for 3D FLAIR, as described in Rydberg J N, et al., Magn Reson Med, 1995; 34(6):868-877, the contents of which are incorporated herein by reference. The IR-SWIET sequence may exhibit T2 weighting from a shorter T2-preparation pulse, which produces hyperintense signal from cortical lesions. The duration of the T2-Prep pulse may be based on the calculated time at which GM and WM signals are equal based on their initial magnetization values. In one embodiment, the T2 preparation before inversion may comprise delay=125 ms; inversion recovery duration=2700 ms; and, improved lesion contrast using T2-Prep=65 ms. The IR-SWIET sequence may use 3D segmented EPI acquisition with bipolar vascular crushing gradients set to crush blood velocities greater than 4 cm/s. The IR-SWIET sequence may also comprise the following acquisition parameters: FOV=245 mm$^2$; res: 0.8*0.86*0.64 mm$^3$; sagittal acquisition; y-SENSE=2.5; z-SENSE=2.5; z-SENSE=2; Proset (for water excitation) 1331 pulse. Several different combinations of acquisition parameters and inversion times listed above may achieve similar results. In one embodiment, the IR-SWIET sequence may be repeated 2-4 times and the results averaged, which may increase the SNR. The average may be a voxel-wise mean or median. In one example, the average may be a voxel-wise median. The IR-SWIET method may also comprise motion correction before averaging and visualization. The images produced by the MRI scanner may be used directly for visualization of cortical lesions.

c. Multicontrast Image Review

In another example, images generated using an IR-SWIET sequence described herein may be viewed alongside one or more MRI sequences to more sensitively and accurately identify cortical lesions. These may include one or more standard clinical MRI sequences such as MP2RAGE, FLAIR, or high-resolution conventional T2*-weighted gradient-echo images. In one example, the IR-SWIET sequence may be combined with a MP2RAGE sequence, a FLAIR sequence, or the combination thereof. In one example, both MP2RAGE and FLAIR sequences are performed. The IR-SWIET sequence may be repeated 2-4 times, and the signal data from the IR-SWIET sequences may be averaged. In one example, the IR-SWIET sequence is repeated twice and the signal data from the repeated sequences are averaged. The average may be a voxel-wise median. A comparison of images generated by the IR-SWIET sequence, and the MP2RAGE or FLAIR sequences or the combination thereof may be used to identify cortical lesions. In particular, the images may be compared side-by-side.

2. MRI Systems for Detecting Cortical Lesions

Provided herein is an MRI system for detecting cortical lesions. The MRI system may perform or may be configured to perform one or more of the MRI methods described herein. The MRI system may comprise a MRI device, which may comprise a magnet system to generate a polarizing magnetic field about at least a portion of a subject arranged in the MRI system, a plurality of gradient coils to apply a gradient field to the polarizing magnetic field, and a radiofrequency (RF) system to apply an RF excitation field to a region of interest in the subject and acquire MR image data therefrom. The MRI system may also comprise a computer system, having a processor and memory, the computer system programmed to perform a pulse sequence described herein that suppresses CSF signals by controlling the MRI device, and acquires signal data generated using the pulse sequence. The computer system may also reconstruct a set of images from the acquired signal data and identify a cortical lesion by analyzing the set of images for a visual signature. The computer system may further determine a neurological disease state using the identification of one or more cortical lesions.

In one embodiment, the MRI system comprises a Philips 3 T ACHIEVA™ Scanner, which may comprise a 32-channel head coil. The Philips scanner may be particularly useful for the IR-SWIET method described herein. In another embodiment, the MRI system comprises a Siemens 3 T scanner. The Siemens scanner may be particularly useful for the DWI method described herein. The MRI system may comprise one or more phased-array coils.

3. Methods of Diagnosing and Evaluating a Neurological Condition

Provided herein is a method to assist in diagnosing and evaluating a neurological condition. The presence of one or more cortical lesions may be indicative of a neurological condition, or may be used in assessing the prognosis or response to treatment of the neurological condition. The neurological condition may be multiple sclerosis (MS), traumatic brain injury, stroke, epilepsy, or any other condition that affects the cerebral cortex. Images produced by the MRI methods described herein may also provide clinically useful information about lesions in other portions of the central nervous system.

The present invention has multiple aspects, illustrated by the following non-limiting examples.

EXAMPLE 1

High-Resolution T2*-Weighted, Cerebrospinal Fluid-Suppressed MR Imaging of Cortical Lesions This example demonstrates that two different approaches based on high-resolution T2*-weighted sequences that suppress CSF signals (the DWI approach and the IR-SWIET approach) are capable of detecting cortical lesions better than existing approaches.

Figure 3:
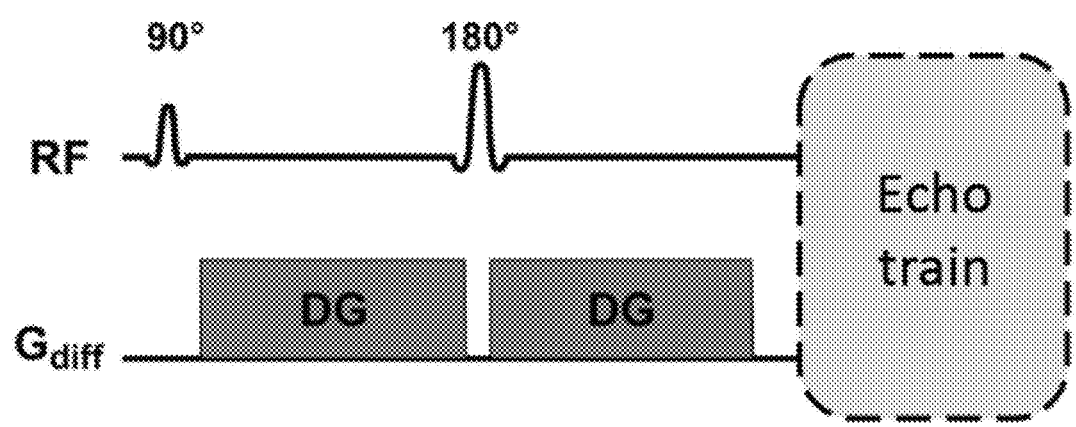
FIG. 3 shows the schematic for a high-resolution Diffusion Weighted Imaging sequence described herein. RF—radiofrequency, DG—diffusion gradient, $G_{diff}$—gradient waveform in the diffusion direction.

FIGS. 1-3 show the schematics for the IR-SWIET and DWI approaches.

Figure 4:
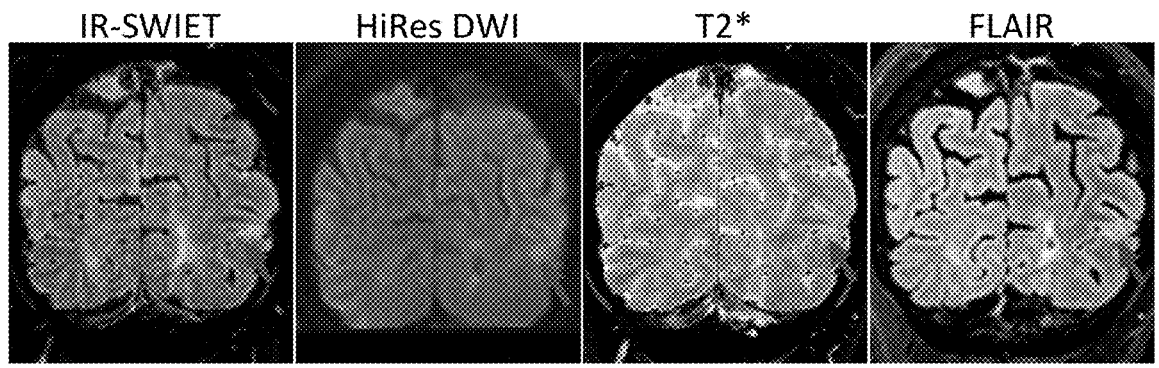
FIGS. 4A-B show that cortical lesions are more conspicuous on images generated using High-Resolution Trace Diffusion-Weighted Imaging and IR-SWIET sequences compared to FLAIR and standard T2*-weighted sequences.
Figure 4:
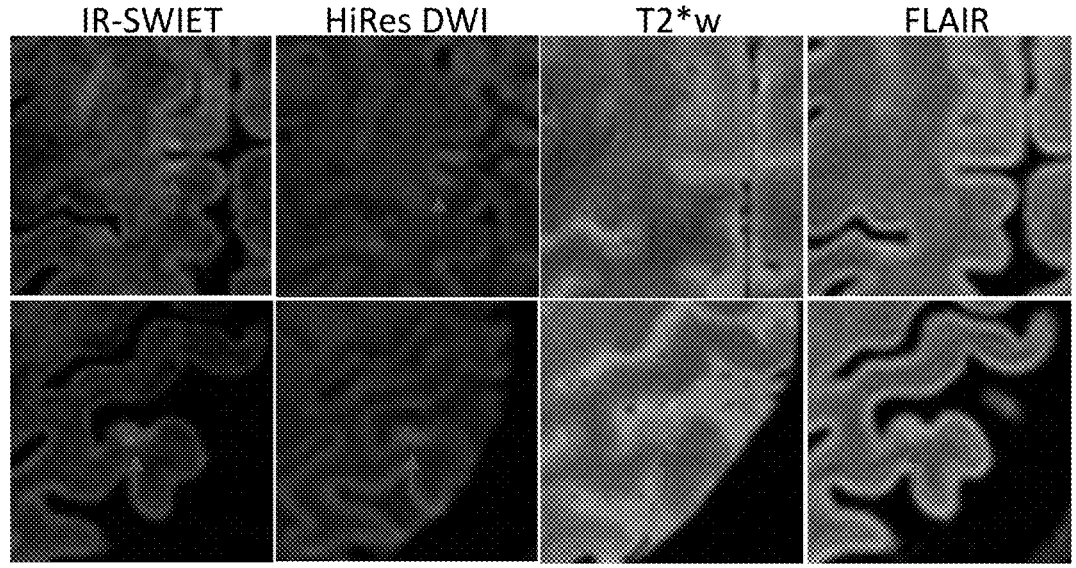

FIG. 4 shows that a T2*-weighted sequence that includes inversion pulse with acquisition at null point of CSF and with T2-preparations (IR-SWIET) and the DWI approach improve the visualization of cortical lesions as compared to a T2*-weighted or FLAIR sequence alone.

EXAMPLE 2

Inversion Recovery Susceptibility Weighted Imaging with Enhanced T2 Weighting (IR-SWIET) for Detecting Multiple Sclerosis Lesions This example demonstrates the design and evaluation of a 3D sequence (IR-SWIET) that suppresses CSF while maintaining T2* contrast with additional T2 weighting for visualizing cortical and white matter lesions in MS. Multiple sclerosis is an inflammatory, demyelinating, and neurodegenerative disease of the central nervous system. Iron deposition visualized through T2*-weighted imaging has been thought to be a surrogate biomarker for different lesion characteristics (Haacke E M, et al., J Magn Reson Imaging 2009; 29(3):537-544). Iron concentration changes have been observed in newly forming lesions of MS patients (Zhang Y, et al., AJNR Am J Neuroradiol 2016:1629-1635), while central veins visualized by SWI or similar approaches may be a distinguishing feature of MS lesions (Sati P, et al., Nat Rev Neurol 2016:714-722).

3D interleaved echo planar imaging (EPI) (Zwanenburg J J, et al., Neuroimage, 2011; 56(4):1902-1907) or spiral imaging (Wu B, et al., Neuroimage 2012; 59(1):297-305) provide rapid SWI of the entire brain with high resolution in a relatively short time. SWI provides important information regarding iron deposition and lesions in multiple sclerosis, but cortical lesions cannot be readily visualized in this method, probably due to the low in-plane resolution or persistent T1-weighting in the acquisition. Similar limitations exist for clinical FLAIR and T1-weighted images which fail to reliably show cortical lesions due to low resolution and lack of adequate T2*-weighting or presence of residual T1-weighting.

We compared cortical lesion visualization independently on IR-SWIET (median signal from 4 acquisitions), magnetization-prepared 2 rapid acquisition gradient echoes (MP2RAGE), double inversion recovery (DIR), susceptibility weighted imaging (SWI), and phase sensitive inversion recovery (PSIR) images for 10 adults with MS. We also identified cortical lesions with a multimodal reading of IR-SWIET (median of 2 acquisitions), MP2RAGE, and fluid attenuated inversion recovery (FLAIR) images for each case. Lesions identified on 3 T images were verified on "gold standard" 7 T T2* and MP2RAGE images.

Methods

Theory and Simulations

The aim was to suppress CSF while maintaining T2 and T2* contrast similar to a 3D SWI sequence. Bloch simulation for SWI (FIGS. 1 and 2) shows the signal evolution for gray matter (GM), white matter (WM), and CSF. T1/T2 and proton density values from literature were used (Stanisz G J, et al., Magn Reson Med 2005; 54(3):507-512; Shin W, et al., Magn Reson Med 2009; 61(4):899-906; Gai N D, et al., J Magn Reson Imaging 2009; 30(3):640-648; Gutteridge S, et al., Magn Reson Med 2002; 47(5):871-879) along with parameters corresponding to 3D SWI (Table 2). Acquisition was performed at steady-state (FIG. 1, arrow).

The SWI sequence was modified to suppress CSF using $90_x$-$180_y(4)$-$90_x$ T2Prep followed by inversion similar to preparation for 3D FLAIR (Rydberg J N, et al., Magn Reson Med, 1995; 34(6):868-877, the contents of which are incorporated herein by reference). Since magnetization for GM recovers at a slower rate than for WM, GM-lesion-WM T2 contrast is compromised at CSF null. To compensate for the lower GM longitudinal magnetization, a shorter duration T2-Prep pulse was introduced prior to EPI acquisition to provide T2-weighting. This T2-Prep duration was based on calculated time at which GM and WM signal are equal based on their initial magnetization values. The final sequence is shown schematically in FIG. 2, along with magnetization evolution. Improved T2-weighting was obtained by acquiring the echo train in a centric fashion.

Data Acquisition

Ten adults with MS and two healthy adults (see Table 1 for cohort details) underwent scans on a 3 T scanner (Philips Achieva 3.0 T; Philips Healthcare, Eindhoven, the Netherlands) equipped with a 32-channel head coil, including optimized IR-SWIET, acquired four times in each scanning session, FLAIR, DIR, PSIR, and SWI (see Table 2 for sequence parameters).

TABLE 1

|  | MS (n = 10) | HV (n = 2) |
|---|---|---|
| Age (years), mean ± standard deviation | 48 ± 6 | 46 ± 11 |
| Sex, female/male | 7/3 | 1/1 |
| Years since symptom onset, mean ± standard deviation | 9 ± 5 |  |
| Clinical subtype |  |  |
| Relapsing Remitting | 8 |  |
| Secondary Progressive | 1 |  |
| Primary Progressive | 1 |  |
| Expanded Disability Status Score, median (range) | 2 (0-6.5) |  |

For the MS cases, previously acquired 3 T MP2RAGE images (3 T Magnetom Skyra, Siemens, Erlangen, Germany, equipped with a 32-channel head coil) and 7 T MP2RAGE and T2*-weighted gradient recalled echo (GRE) images (7 T whole-body research system, Siemens, equipped with a single-cannel transmit, 32-channel phased array receive head coil) were also used for comparison. 7 T scans were acquired 1-7 months (median 4 months) before the 3 T scans.

TABLE 2

|  | 3T | | | | | | 7T | |
|---|---|---|---|---|---|---|---|---|
|  | IR-SWIET[1] | DIR[2] | MP2RAGE[3] | SWI[4] | FLAIR[5] | PSIR[6] | MP2RAGE | $T_2$* wGRE[7] |
| Orientation | Sagittal | Sagittal | Sagittal | Sagittal | Sagittal | Axial | Axial | Axial |
| Voxel dimensions (mm) | 0.8 × 0.8 (reconstructed at 0.64 × 0.64) | 1.2 × 1.2 | 1 × 1 | 0.54 × 0.57 | 1 × 1 | 0.5 × 0.53 | 0.5 × 0.5 | 0.5 × 0.5 |
| Slice thickness (mm) | 0.64 | 0.65 | 1 | 0.55 | 0.76 | 2 | 0.50 | 0.50 |
| TI (ms) | 2650 | 2550/450 | 700/2500 | NA | 1650 | 400 | 800/2700 | NA |
| TR/TE (ms) | 58.32 | 5500/203 | 5000/2.9 | 54/29 | 4800/321 | 10010/17 | 6000/5 | 4095/11.4, 22.5, 33.6, 44.7, 55.8 |

TABLE 2-continued

|  | 3T | | | | | | 7T | |
| --- | --- | --- | --- | --- | --- | --- | --- | --- |
|  | IR-SWIET[1] | DIR[2] | MP2RAGE[3] | SWI[4] | FLAIR[5] | PSIR[6] | MP2RAGE | $T_2$ * wGRE[7] |
| Flip angle (°) | 10 | 90 | 4/5 | 10 | 90 | 90 | 4/5 | 70 |
| Scan time (min:sec) | 5:08 | 10:44 | 8:16 | 4:15 | 4:55 | 8:30 | 10:32 | 11:26 (×3) |

Table 2.
Sequence Parameters.
[1]Inversion recovery susceptibility weighted imaging with enhanced T2 weighting,
[2]Double inversion recovery,
[3]Magnetization-prepared rapid gradient echo,
[4]Susceptibility weighted imaging,
[5]Fluid-attenuated inversion recovery,
[6]Phase-sensitive inversion recovery.
TI—inversion time,
TR—repetition time,
TE—echo time.

Image Processing

MP2RAGE 3 T and 7 T processing to generate uniform images was performed on the respective scanners as a part of the Siemens research sequence package (Work-in-Progress Package #900D). IR-SWIET repetitions were coregistered (ANTS, Advanced Normalization Tools, github.com/ANTsX/ANTs), and the voxel-wise median of the first 2 or all 4 acquisitions was generated. The median was used, rather than the mean, to decrease the contribution of outlier values that may arise due to noise or motion. All images were aligned to the 7 T MP2RAGE uniform denoised images using linear coregistration (AFNI, Analysis of Functional NeuroImages, afni.nimh.nih.gov).

Lesion Identification and Comparison

Cortical lesions were manually segmented using the software package Display (github.com/BIC-MNI/Display) developed at the McConnell Brain Imaging Center of the Montreal Neurological Institute.

Figure 5:
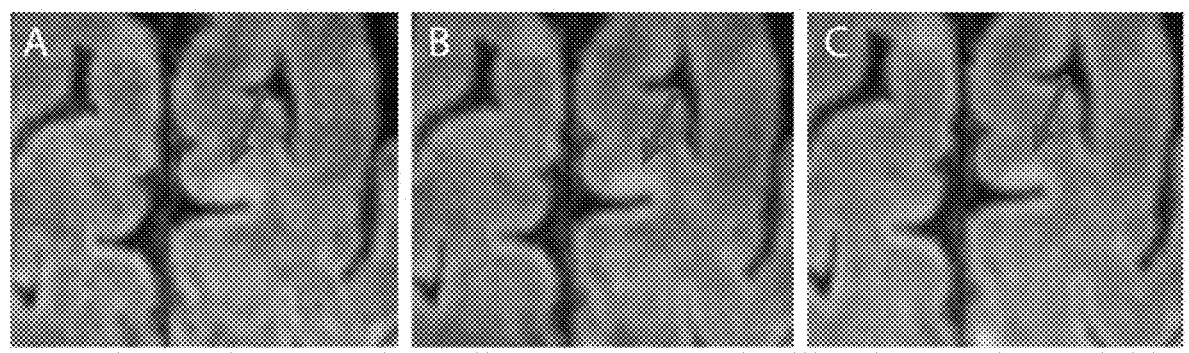
FIGS. 5A-C show that cortical lesion conspicuity is improved by averaging multiple acquisitions of inversion recovery susceptibility weighted imaging with enhanced T2 weighting (IR-SWIET) images.

Cortical lesions were identified and marked on all 3 T images by an experienced neurologist (with >3 years' experience in cortical lesion segmentation). Cortical lesions were identified on 3 T IR-SWIET single acquisition (IR-SWIET×1), IR-SWIET median of two acquisitions (IR-SWIET×2), IRSWIET median of four acquisitions (IR-SWIET×4, see FIG. 5 and Table 3 for comparison of IRSWIET averages), DIR, PSIR, FLAIR, SWI, and MP2RAGE images independently in random order, with at least 1 week in between analysis of each sequence from the same subject.

In addition, two 3 T multicontrast reads were performed for each subject: (1) IR-SWIET×2, MP2RAGE, FLAIR; (2) DIR, MP2RAGE, FLAIR. Cortical lesions were segmented on 7 T images using both MP2RAGE and T2*w GRE images. This segmentation was done by 2 raters independently (one neurologist with >3 years' experience and one neuroradiologist with >15 years' experience), followed by a consensus read by both raters. On 3 T and 7 T images, cortical lesions were classified as leukocortical, intracortical, or subpial. Lesion volume was calculated for each cortical lesion identified on 7 T images using the MP2RAGE images.

Following identification of cortical lesions on all 3 T images, each marked lesion was compared to the 7 T images used as a "gold standard" for cortical lesion segmentation. Each lesion was classified as a true cortical lesion, a juxtacortical lesion, a false positive if no correlate was seen on 7 T images, or a false negative cortical lesion if a lesion was seen on 7 T images only in retrospect. Lesions identified on 3 T images that were out of the field of view (FOV) on the 7 T images (which do not cover the inferior regions of the temporal and occipital lobes) were classified as out-of-FOV and were not included in the quantitative analyses of lesion detection. For lesion detection analyses, cortical lesion subtype was determined based on the appearance of each lesion at 7 T, as subtyping was difficult at 3 T.

Purely intracortical (i.e., non-subpial) lesions seen on 7 T images were virtually undetected on all of the 3 T images, with only 3 intracortical lesions identified on 3 T images for all 10 MS cases. Thus, intracortical lesions are included in the total cortical lesion analysis but were not separately analyzed.

Contrast to noise ratio (defined as (SI1−SI2)/(SI1+SI2)) was measured in 30 lesions (intracortical, leukocortical, and periventricular), which were depicted on all sequences after registration and reformatting.

TABLE 3

|  | Subpial lesions | | | Leukocortical lesions | | | Total cortical lesions | | |
| --- | --- | --- | --- | --- | --- | --- | --- | --- | --- |
|  | Total | Median (range) | Sensitivity (mean ± SEM) | Total | Median (range) | Sensitivity (mean ± SEM) | Total | Median (range) | Sensitivity (mean ± SEM) |
| IR-SWIET × 4 | 101 | 5 (0-38) | 29 ± 8% | 110 | 10 (0-35) | 27 ± 6% | 217 | 15 (5-56) | 28 ± 3% |
| IR-SWIET × 2 | 85 | 2 (0-41) | 20 ± 5% | 98 | 10 (0-31) | 25 ± 5% | 189 | 14 (2-49) | 23 ± 4% |
| IR-SWIET | 62 | 3 (0-26) | 18 ± 5% | 76 | 6 (0-22) | 21 ± 7% | 147 | 14 (1-33) | 20 ± 4% |

No significant differences were found between the number of lesions or sensitivity vs 7T for subpial, leukocortical, or total cortical lesions.
IR-SWTET—inversion recovery susceptibility weighted imaging with enhanced T2 weighting (×2—average of 2 acquisitions, ×4—average of 4 acquisitions).

Statistics

The Friedman test was used to compare detected lesion number, sensitivity, and volume between individual sequences. Spearman correlation coefficients were calculated when comparing number of subpial lesions identified on 3 T vs 7 T. A linear mixed effects model was used to determine the effect of 3 T sequence on subpial classification accuracy, with subject included in the model as a random intercept. Post-hoc pairwise comparisons between individual sequences and IR-SWIET×4 as well as comparisons between the two multimodal reads were performed. As this was an exploratory study, p-values, when <0.05, were reported directly without adjustment for multiple comparisons.

Results

MS Lesions were Conspicuous on IR-SWIET Images

Figure 6:
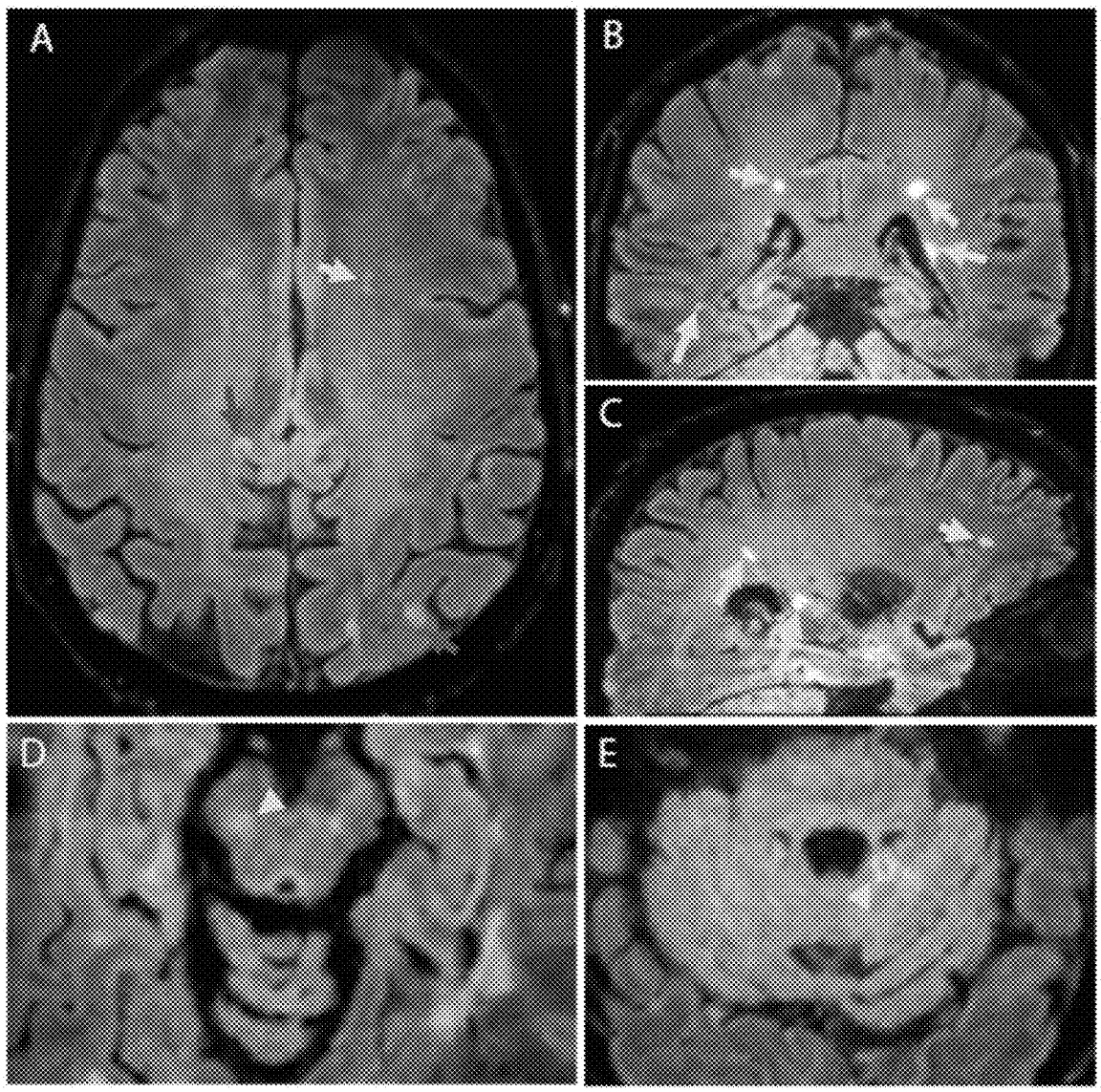
FIGS. 6A-E show Inversion recovery—susceptibility weighted imaging with enhanced T2 weighting (IRSWIET)

On IR-SWIET images, there was low contrast between gray and white matter, and the CSF signal was effectively suppressed. MS lesions in the white matter, deep gray matter, brainstem, and cortex are clearly visualized (FIG. 6). In many cases, central veins, which are a hallmark of MS lesions, could be seen within lesions (FIGS. 6C,E). However, there was very little differentiation between gray and white matter, making distinction between juxta- and leukocortical lesions difficult based solely on the IR-SWIET images.

CNR is Improved on IR-SWIFT

Table 4 shows CNR measurements (weighted by size) obtained from the three lesion sub-types for all sequences on a subset of 3 MS cases. Table 5 provides total lesion volumes analyzed on the same subset of 3 cases.

TABLE 4

CNR measured for each sequence and lesion type relative to surrounding tissue

|  | IR-SWIET | SWI | DIR | FLAIR | MP2RAGE |
|---|---|---|---|---|---|
| Intracortical | 0.260 | 0.061 | 0.339 | 0.159 | −0.048 |
| Leukocortical | 0.251 | 0.069 | 0.235 | 0.145 | −0.202 |
| Periventricular | 0.513 | 0.050 | 0.543 | 0.159 | 0.251 |

TABLE 5

Lesion volume analyzed for each sequence. Differences in measured volumes are due to partial volume averaging and due to difficulty in defining lesion boundaries

|  | IR-SWIET | SWI | DIR | FLAIR | MP2RAGE |
|---|---|---|---|---|---|
| Intracortical | 857 | 791 | 877 | 853 | 894 |
| Leukocortical | 2487 | 2304 | 1836 | 1990 | 1594 |
| Periventricular | 660 | 722 | 679 | 826 | 478 |

IR-SWIET and DIR showed similar contrast for all three types of lesions studied, while SWI showed the poorest contrast. Intracortical lesions on DIR, although hyperintense compared with WM/CSF, were sometimes almost isointense with surrounding unaffected GM. MP2RAGE had comparable contrast as IR-SWIET and DIR for leukocortical lesions but poorer contrast for intracortical lesions due to hypointensity and proximity to suppressed CSF.

More Subpial Lesions were Detected on IR-SWIET

Figure 7:
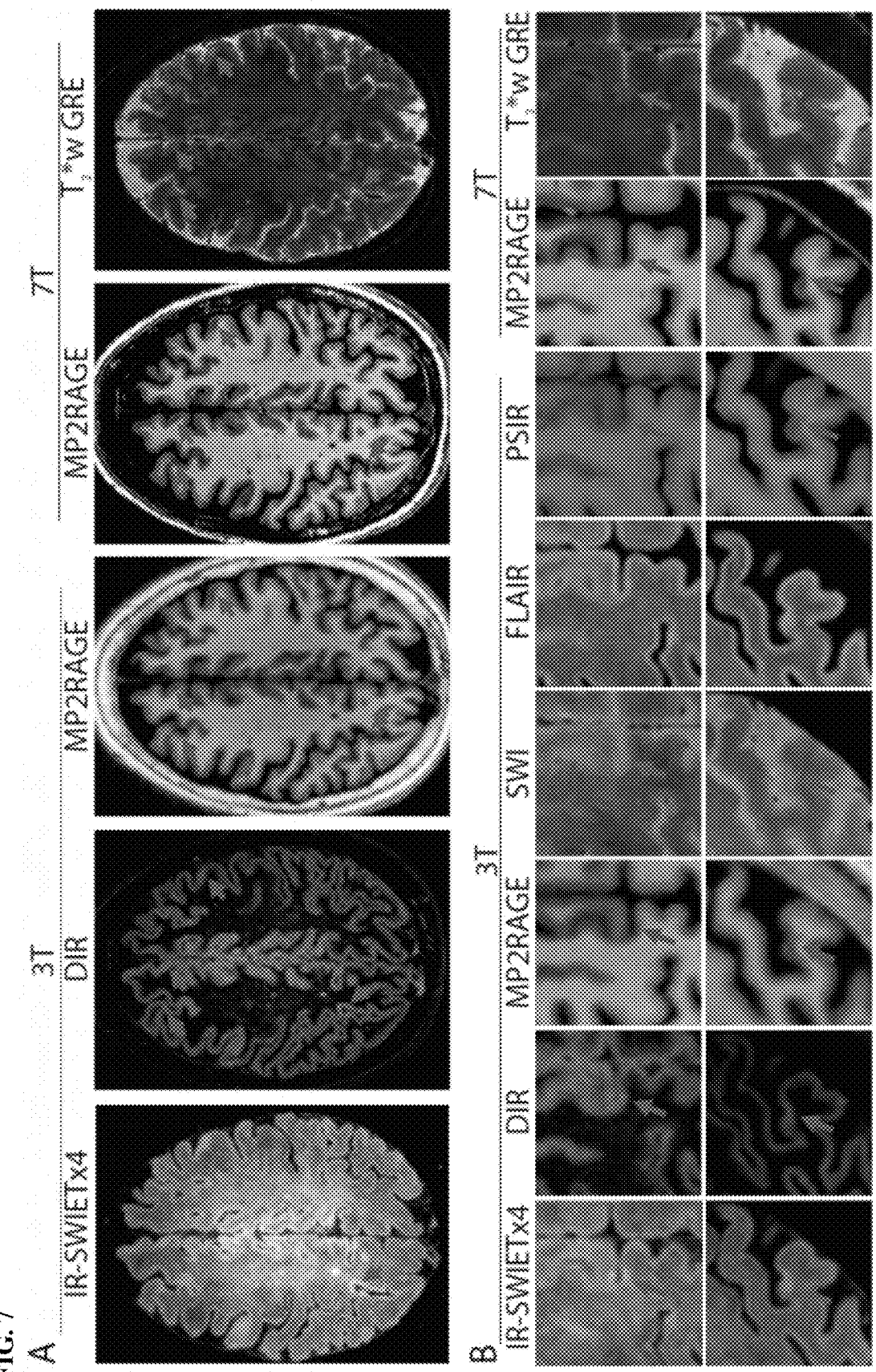
FIGS. 7A-B show that IR-SWIET improves subpial lesion detection.
Figure 8:
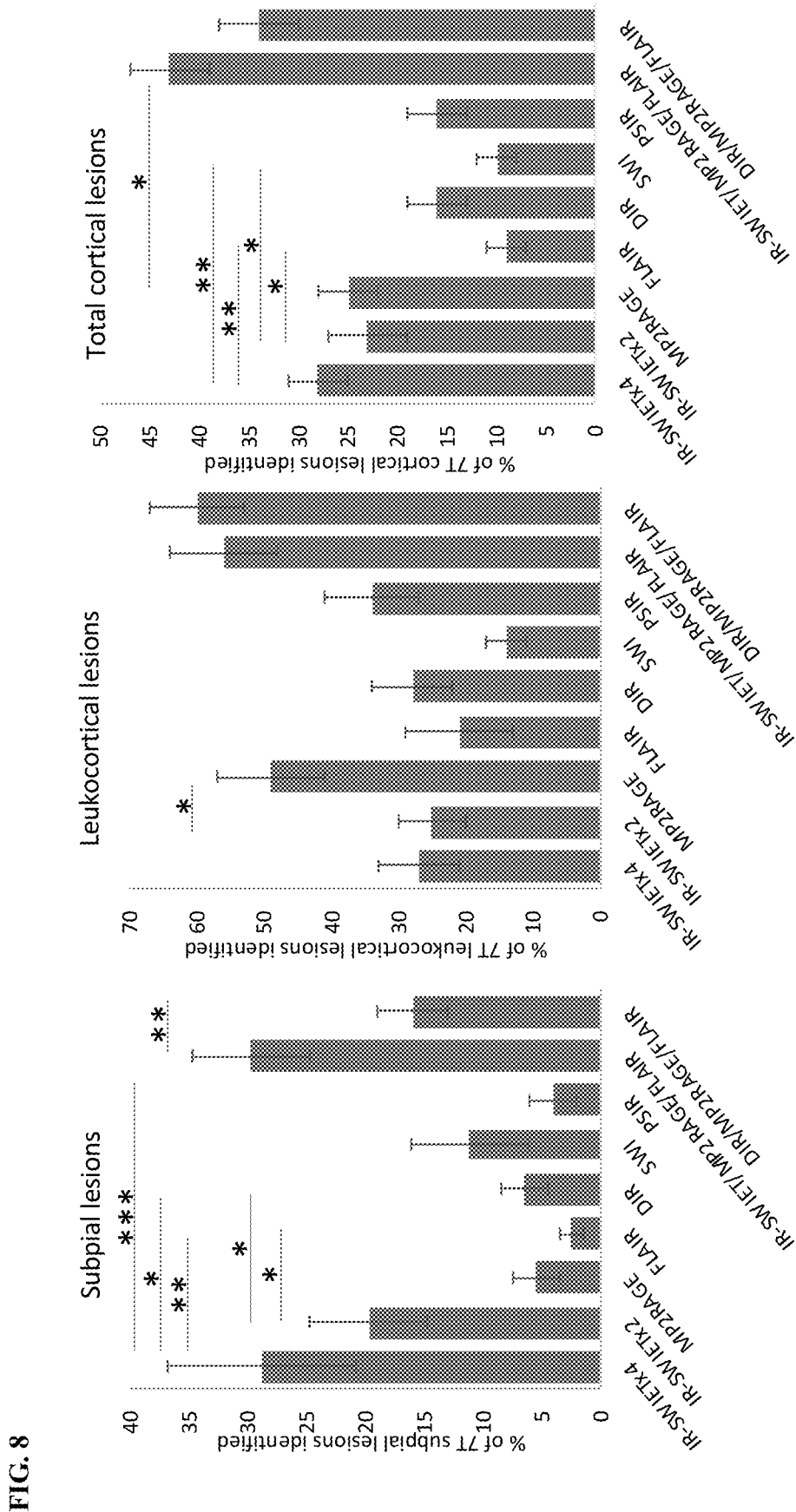
FIG. 8 shows that IR-SWIET improves subpial lesion detection. Quantification of sensitivity of individual 3 T sequences and 3 T multicontrast reads compared to lesions identified on 7 T images. *=p<0.05, =p<0.01, *=p<0.001, IR-SWIET—inversion recovery susceptibility weighted imaging with enhanced T2 weighting (×2—median of 2 acquisitions, ×4—median of 4 acquisitions), DIR—double inversion recovery, MP2RAGE—magnetization-prepared rapid gradient echo, SWI—susceptibility weighted imaging, FLAIR—fluid-attenuated inversion recovery, PSIR—phase sensitive inversion recovery.

Images from 10 adults with MS were used to identify cortical lesions independently on IRSWIET×2 and ×4, other state-of-the-art sequences used to detect cortical lesions (DIR, PSIR), and standard clinical MRI sequences (MP2RAGE, FLAIR, SWI). A similar number of total cortical lesions were identified on each of the individual 3 T sequences (Table 6, FIGS. 7-8).

TABLE 6

| | Subpial lesions | | | Leukocortical lesions | | | Total cortical lesions | | |
|---|---|---|---|---|---|---|---|---|---|
| | Total | Median (range) | Sensitivity (mean ± SEM) | Total | Median (range) | Sensitivity (mean ± SEM) | Total | Median (range) | Sensitivity (mean ± SEM) |
| IR-SWIET × 4 | 101 | 5 (0-38) | 29 ± 8% | 110 | 10 (0-35) | 27 ± 6% | 217 | 15 (5-56) | 28 ± 3% |
| IR-SWIET × 2 | 85 | 2 (0-41) | 20 ± 5% | 98 | 10 (0-31) | 25 ± 5% | 189 | 14 (2-49) | 23 ± 4% |
| MP2RAGE | 36 | 1 (0-13) | 5 ± 2% | 172 | 14 (0-44)† | 49 ± 8%† | 216 | 17 (1-54) | 25 ± 3% |
| FLAIR | 17 | 0 (0-7)**,† | 2 ± 1%*,† | 51 | 5 (0-11) | 21 ± 8% | 68 | 5 (0-17)**,† | 9 ± 2%**,† |
| DIR | 28 | 1 (0-15)* | 6 ± 2%*,† | 95 | 12 (0-20) | 28 ± 6% | 128 | 14 (0-28) | 16 ± 3% |
| SWI | 42 | 2 (0-16) | 11 ± 5%* | 44 | 4 (0-10) | 14 ± 3% | 84 | 6 (0-25)**,† | 10 ± 2%**,† |
| PSIR | 13 | 1 (0-6)***,† | 4 ± 2%* | 96 | 10 (0-17) | 34 ± 7% | 113 | 13 (0-21) | 16 ± 3% |
| IRSWIET × 2/ MP2RAGE/ FLAIR | 147 | 5 (0-63)### | 30 ± 5%##,‡‡ | 225 | 17 (0-53) | 56 ± 8% | 380 | 24 (0-119)### | 43 ± 4%##,‡ |
| DIR/ MP2RAGE/ FLAIR | 83 | 3 (0-33) | 16 ± 3%## | 231 | 18 (0-52)# | 60 ± 7%# | 300 | 24 (1-72) | 34 ± 4%## |
| 7T | 380 | 21 (6-124) | | 360 | 26 (1-84) | | 785 | 58 (17-201) | |

*$p < 0.05$ vs IR-SWIET × 4,
**$p < 0.01$ vs IR-SWIET × 4,
*** $p < 0.001$ vs IRSWIET × 4,
† $p < 0.05$ vs IR-SWIET × 2,
†† $p < 0.01$ vs IR-SWIET × 2,
‡ $p < 0.05$ vs DIR/MP2RAGE/FLAIR,
‡‡ $p < 0.01$ vs DIR/MP2RAGE/FLAIR,
$p < 0.05$ vs MP2RAGE,
$p < 0.01$ vs MP2RAGE,
$p < 0.001$ vs MP2RAGE.

IR-SWIET—inversion recovery susceptibility weighted imaging with enhanced T2 weighting (×2—average of 2 acquisitions, ×4—average of 4 acquisitions),
DIR—double inversion recovery,
MP2RAGE—magnetization prepared rapid gradient echo,
SWI—susceptibility weighted imaging,
FLAIR—fluid-attenuated inversion recovery,
PSIR—phase-sensitive inversion recovery,
GRE—gradient recalled echo.

While IR-SWIET did not improve detection of leukocortical lesions, there was a significant improvement in subpial lesion detection. A total of 101 true positive subpial lesions (per case median 5, average sensitivity vs. 7 T 29%) were detected on IR-SWIET×4, compared to 36 (median 1, sensitivity 5%, sensitivity vs IR-SWIET×4 p=0.07) on MP2RAGE and 28 (median 1, sensitivity 6%, p<0.05) on DIR. The percentage of lesions classified as false positive did not differ between sequences. No cortical lesions were detected on any combination of IR-SWIET images in either of the two healthy volunteers who were scanned. In addition, more cases had at least one subpial lesion on IR-SWIET×4 (9 of 10 cases) than any of the other 3 T sequences: MP2RAGE (6/10), FLAIR (4/10), DIR (6/10), SWI (7/10), and PSIR (5/10).

Inclusion of IR-SWIET in Multicontrast Identification of Cortical Lesions Improved Subpial Lesion Detection To simulate a real-world scenario in which multiple image types are used to identify cortical lesions, we identified cortical lesions on two multicontrast reads: IR-SWIET×2, MP2RAGE, and FLAIR and DIR, MP2RAGE, and FLAIR. IR-SWIET×2 was used instead of IR-SWIET×4 as the improvement in subpial lesion sensitivity between the two was small and the shorter scan time of IR-SWIET×2 (~10 min vs ~20 min) is more clinically feasible. We compared the lesions identified on the 2 multimodal reads with lesions identified on 3 T MP2RAGE alone to determine if inclusion of IR-SWIET or DIR, neither of which is used routinely on clinical MRI scans, improves subpial sensitivity over the more standard 3 T MP2RAGE sequence. The multimodal read of IR-SWIET×2, MP2RAGE, and FLAIR improved average cortical lesion sensitivity vs MP2RAGE alone (43% vs 25%, p<0.05). The IR-SWIET×2/MP2RAGE/FLAIR multimodal read was also more sensitive for subpial lesions (30%) compared to DIR/MP2RAGE/FLAIR (16%, p<0.01) or MP2RAGE alone (5%, p<0.01) (Table 6, FIGS. 7,8). At least one subpial lesion was detected in more cases on the multimodal read that included IR-SWIET (9/10) than on the read that included DIR (8/10).

Contribution of Lesion Size to Cortical Lesion Detection

Figure 9:
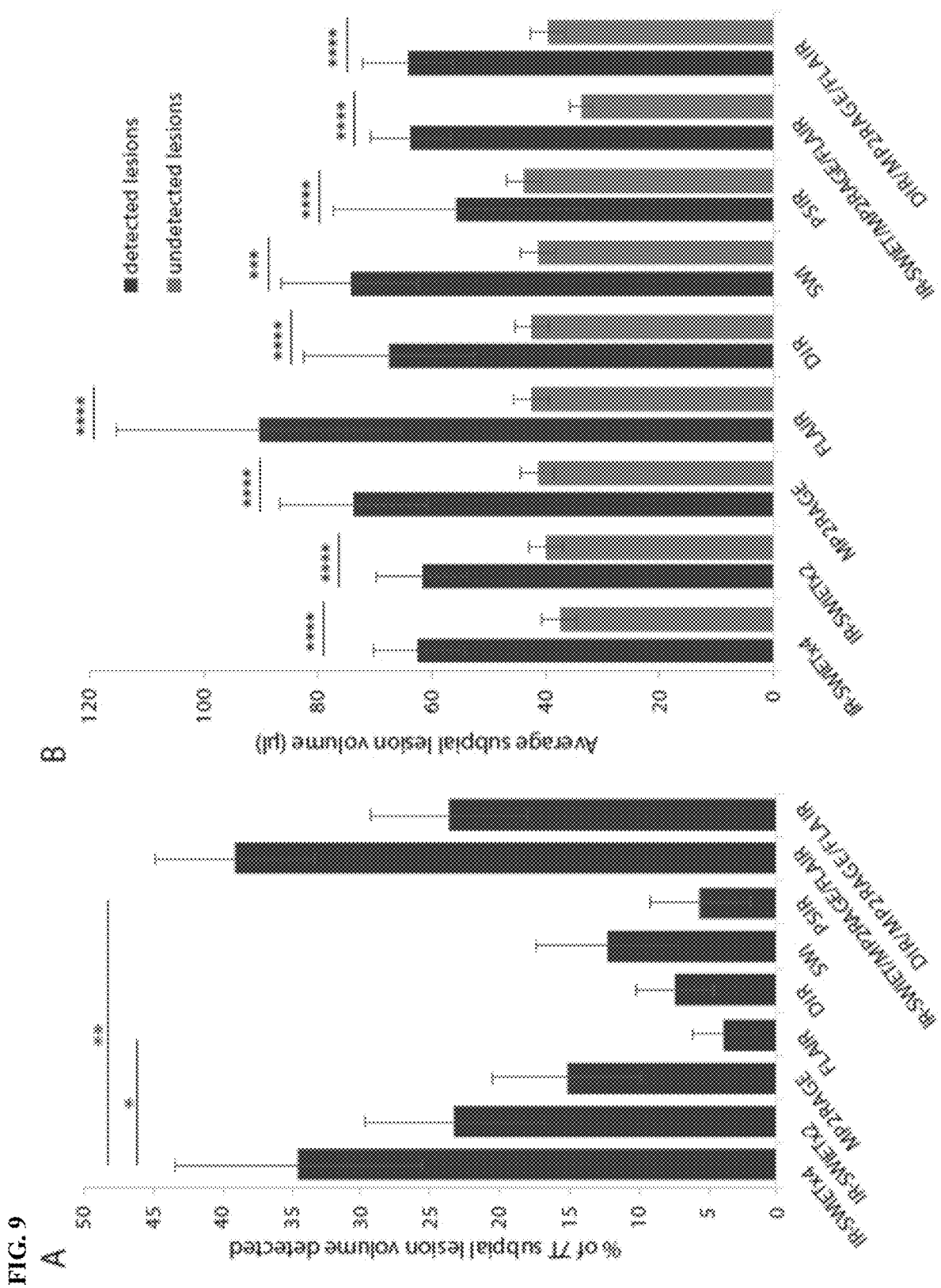
FIGS. 9A-B show detection of subpial lesions by volume.
Figure 10:
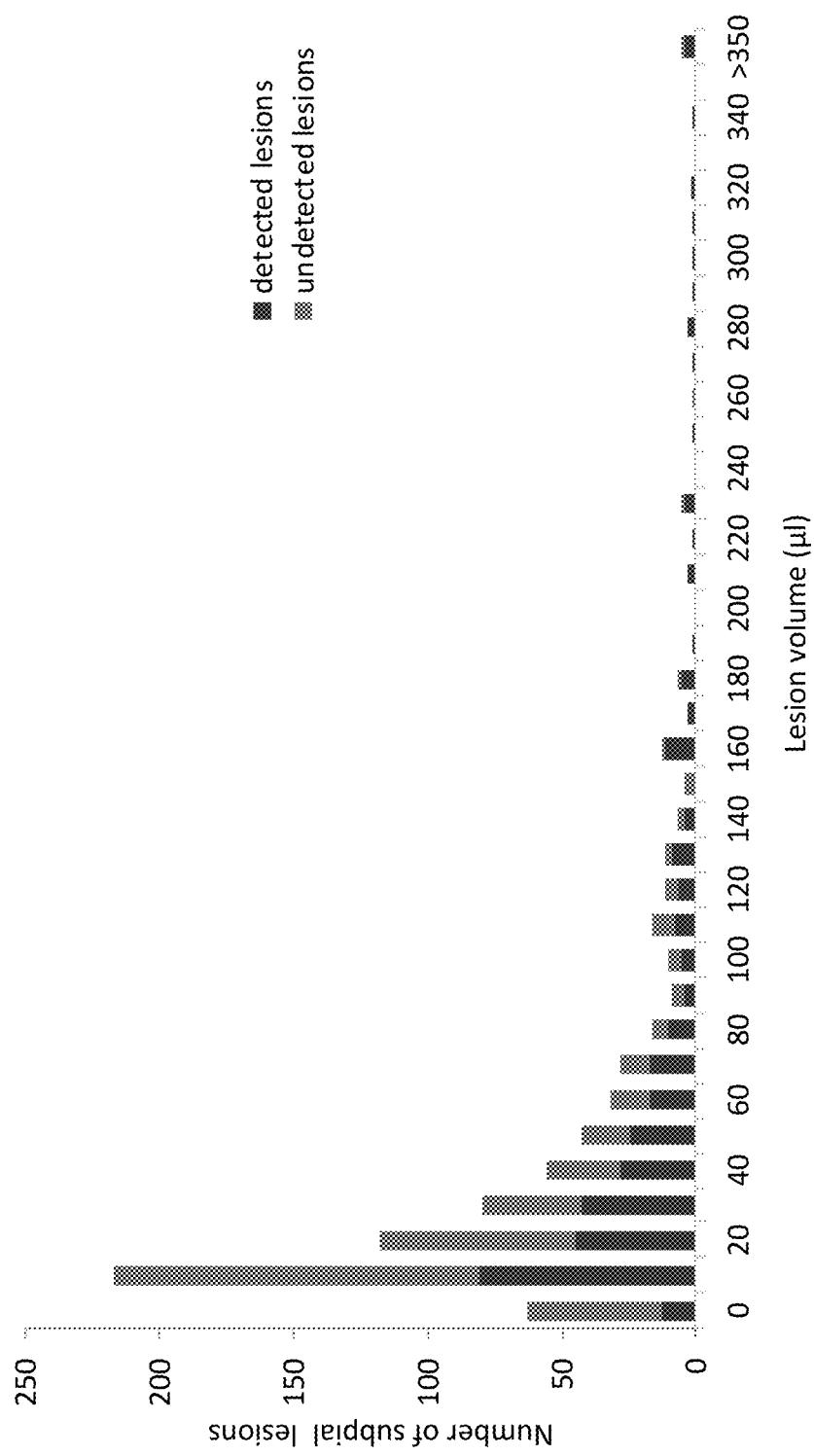
FIG. 10 shows that the proportion of detected subpial lesions on IR-SWIET images increased with lesion volume.

Although IR-SWIET increases the number of detected subpial lesions substantially, the number of subpial lesions identified on 3 T remained lower than the number detected on 7 T. A maximum of 30% of subpial lesions identified on 7 T images were detected on 3 T images using a combination of IR-SWIET×2, MP2RAGE, and FLAIR. We investigated the impact of cortical lesion size measured on 7 T MP2RAGE on the detectability of lesions at 3 T. For each sequence, the average size of detected lesions was greater than the average size of undetected lesions (p<0.001 for each sequence, FIG. 9). When sensitivity of each of the 3 T sequences for subpial lesions was calculated in terms of cortical lesion volume rather than number, we found a similar relationship between the 3 T sequences, with generally higher sensitivity when calculated by volume, likely due to higher sensitivity for larger subpial lesions (FIG. 9). There was no difference between the average size of detected lesions among individual 3 T sequences (FIG. 9). The proportion of detected subpial lesions on IR-SWIET images increased with lesion volume (FIG. 10).

IR-SWIET Improves Subpial Lesion Classification

Figure 11:
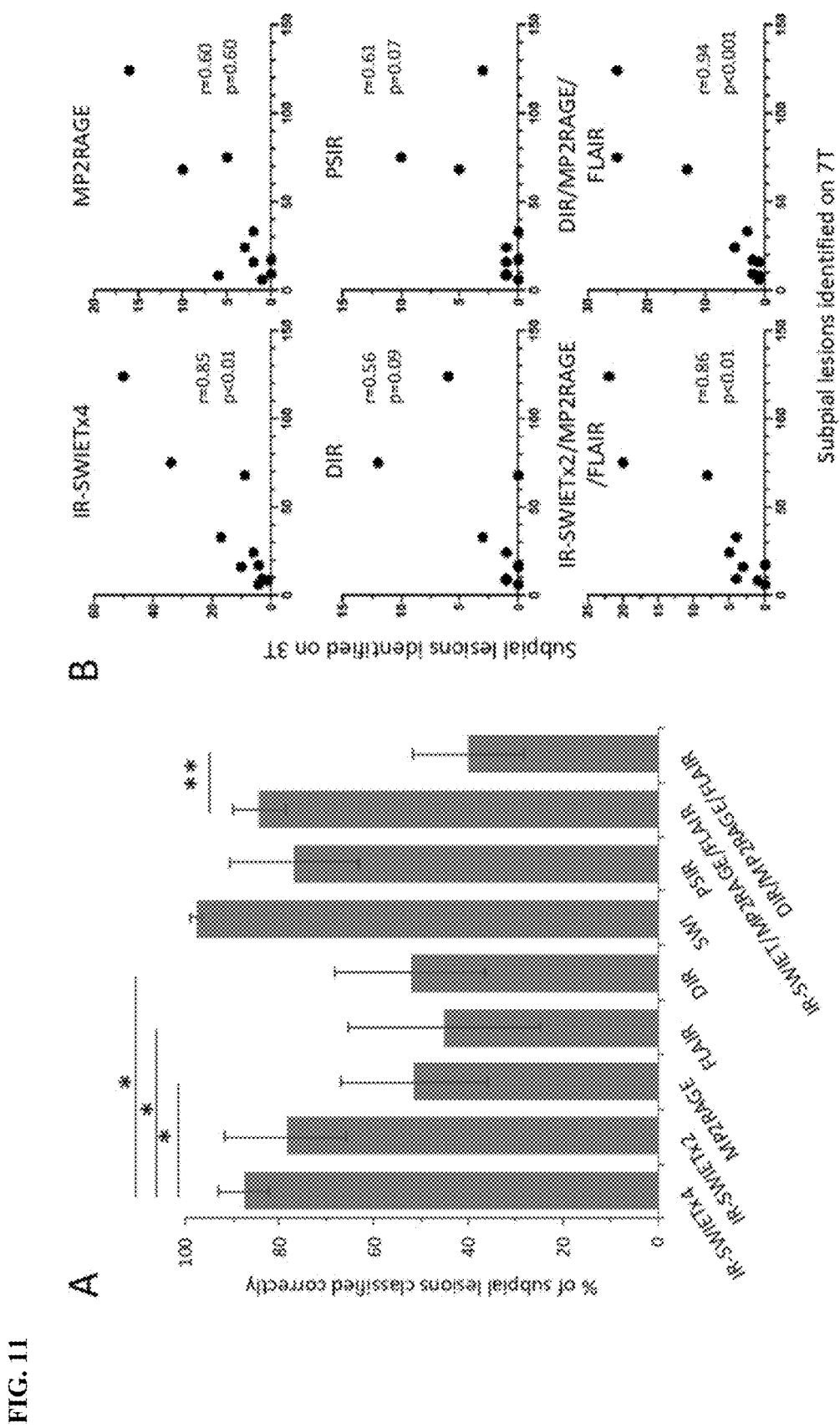
FIGS. 11A-B show that IR-SWIET improves subpial classification and 3 T-7T subpial correlation.

Cortical lesion subtype categorization was done for all of the above analyses based on 7 T images. Cortical lesion subtype was also determined on 3 T images. We determined the percentage of subpial lesions identified on images from each 3 T sequence that were correctly classified as subpial on the 3 T read. On IR-SWIET×4, 88±5% of identified subpial lesions were categorized correctly, vs 79±13% on IR-SWIET×2, 52±16% on MP2RAGE (p<0.01 vs IR-SWIET×4), 45±20% on FLAIR (p<0.01), 53±16% on DIR (p<0.01), 98±1% on SWI (p=0.58), and 77±14% on PSIR (p=0.50) (FIG. 11A). On the IR-SWIET×2/MP2RAGE/FLAIR multimodal read, an average of 84±6% of the detected subpial lesions were correctly classified, versus only 40±12% on the DIR/MP2RAGE/FLAIR multimodal read (p<0.01) (FIG. 11A). Less than 5% of true cortical lesions were misclassified as subpial on any of the individual sequence or multimodal reads.

IR-SWIET Improves 3 T-7T Subpial Correlation

We next examined the relationship between the number of subpial lesions identified on 7 T and the number of lesions identified as subpial on each of the 3 T sequences and the two multimodal reads. False positive and incorrectly classified lesions identified on 3 T were included in this analysis. For the single 3 T sequences, correlation was highest for IR-SWIET×2 (r=0.89, p<0.01). Correlations for other sequences were as follows: IR-SWIET×4 (r=0.85, p<0.01), SWI (r=0.70, p<0.05), FLAIR (r=0.70, p<0.05), PSIR (r=0.61, p=0.07), MP2RAGE (r=0.60, p=0.07), and DIR (r=0.56, p=0.09) (FIG. 13B). The correlation for each of the multimodal reads were similarly high (r=0.86, p<0.01 for IR-SWIET×2/MP2RAGE/FLAIR and r=0.94, p<0.001 for DIR/MP2RAGE/FLAIR) (FIG. 11B).

Discussion

In this study, we report the development and optimization of a new MRI sequence, IR-SWIET, with high-resolution, CSF-suppressed T2* weighted images for better visualization of MS cortical lesions, especially subpial lesions, at 3 T. White matter, deep gray matter, brainstem, and cerebellar lesions are also visible on IR-SWIET images at 3 T. In addition, central veins are clearly seen in white matter and infratentorial lesions. While the sequence was developed and tested in MS, we expect that it will have broad applicability for detection and characterization of a wide range of central nervous system disorders in which the cortex may be affected: potentially including infarction, neoplasm, epilepsy, and congenital/developmental anomalies.

Being EPI based, IR-SWIET could exhibit sensitivity to spatial and temporal variations in B0 field homogeneity caused by susceptibility effects and time-varying eddy currents. Reducing scan time or using dynamic correction techniques can help ameliorate such effects. Employing multiple T2-Prep pulses only modestly increased SAR to 8% of the allowed maximum for a person of average weight.

Accurate optimization for IR-SWIET parameters based on Bloch simulation is confounded by the range of T1/T2 values for WM and GM reported in literature (Bojorquez J Z, et al., Magn Reson Imaging 2017; 35:69-80). Different combinations of parameters (including shorter shot duration) are possible albeit with slightly different CNR. In addition, combining magnitude and phase images could provide additional information on lesion characterization, similar to SWI.

CNR as defined here does not change substantially with increased scan time. This was verified for SWI with NSA=2 instead of 1.

In MS, when cortical lesion identification was compared between IR-SWIET and other 3 T methods, we found that more leukocortical lesions were identified with MP2RAGE than with IR-SWIET. Most of the leukocortical lesions seen on MP2RAGE were visible in retrospect on IR-SWIET. These lesions were likely missed on the initial IR-SWIET review due to the lack of cortex-white matter contrast on these images, leading to misclassification of leukocortical lesions as juxtacortical or subcortical lesions, which were not counted.

In contrast, subpial lesion sensitivity was higher for IR-SWIET than for FLAIR, DIR, SWI, and PSIR. Although there was no statistical difference for the comparison with MP2RAGE, our qualitative impression, which might be borne out quantitatively in a larger study, is that subpial lesions are less conspicuous on MP2RAGE (example in FIG. 11). In addition, more subpial lesions were identified on a multimodal read that included IR-SWIET, MP2RAGE, and FLAIR compared to the multimodal read that included DIR, MP2RAGE, and FLAIR, and more cases were found to have subpial lesions with IR-SWIET, both on individual sequence and multimodal reads. Finally, subpial lesion classification was much more accurate using IR-SWIET×2, MP2RAGE, and FLAIR than with DIR, MP2RAGE, and FLAIR.

Nevertheless, the sensitivity of any combination of the 3 T scans for subpial lesions remained low compared to 7 T MP2RAGE (at most 30% with the IR-SWIET×2, MP2RAGE, and FLAIR multimodal read). This is to some extent expected given the improvement in signal-to-noise and contrast-to-noise ratios at ultra-high field, and differences in imaging resolution (0.5 mm isotropic sequences at 7 T vs 0.8-1 mm in plane resolution at 3 T). In addition, the total acquisition time was much higher on 7 T compared to 3 T: a total of 1 hr 30 min for 7T vs 25 min for 3 T (IR-SWIET×2, MP2RAGE, and FLAIR). While some of the lesions seen on 7 T were likely missed on 3 T due to their small size, other lesions were likely missed due to low contrast between some cortical lesions and normal appearing gray matter. Finally, the 7 T "gold standard" lesions were identified by two raters vs. only one rater for the 3 T images. Even at 7 T, there is significant interrater variability, usually due to lesions missed by a single rater but confirmed as true lesions on a consensus read.

Despite the missed subpial lesions on 3 T images, the correlation between the number of subpial lesions identified on IR-SWIET images and the number identified on 7 T images was high compared to other 3 T sequences. This comparison included false positive 3 T lesions and lesions misclassified as subpial on 3 T, and thus simulates a scenario in which no 7 T gold standard exists for comparison. Given the close correlation between 3 T and 7T subpial lesion number using IR-SWIET and the improved accuracy of subpial classification using this method, associations between subpial lesion number measured on 3 T IR-SWIET and clinical and MRI metrics are likely to be similar to what would be found if subpial lesions were measured on 7 T images, but with the advantages that 3 T MRI is much more accessible in a clinical setting, total scan time is much shorter, and whole-brain coverage is more easily attained.

The focus in this study was on cortical lesion visualization, but white matter and brainstem lesions are also very prominent on IR-SWIET images, as are central veins within lesions. Further dedicated analysis into the utility of this sequence more broadly for MS—where it could potentially substitute for FLAIR and/or susceptibility-weighted imaging—as well as for other conditions, is warranted. In addition, phase images, which were not analyzed here, or a combination of phase and magnitude images, may provide additional information on lesion characterization. Finally, since T1 relaxation plays a role in the IR-SWIET contrast mechanism, the utility of post-gadolinium IR-SWIET acquisition for detection of both parenchymal and leptomeningeal enhancement could also be explored.

In summary, IR-SWIET, when combined with a T1-weighted sequence such as MP2RAGE, allows effective cortical lesion visualization and is much more feasible than 7T methods. We favor an average of two IR-SWIET acquisitions for the best balance of subpial lesion sensitivity and scan time. Associations between subpial cortical lesions, disability, and progressive forms of MS can now be determined in much larger cohorts of patients than has been possible with 7 T and with much higher sensitivity and accuracy than has been possible with current 3 T methods. Cortical lesions detected with IR-SWIET could also be incorporated into clinical trials, which may be essential as we do not currently know if drugs that are effective at inhibiting white matter lesion formation also prevent subpial cortical lesion formation. In addition, cortical demyelination has been studied mainly in the context of MS and there is some evidence that it may be specific to MS, but IR-SWIET could be used to study larger cohorts with other inflammatory and noninflammatory brain diseases to determine how specific subpial demyelination is to MS. Ultimately, IR-SWIET could be incorporated into clinical scans to improve accuracy of MS diagnosis and prognosis, and help to measure response to treatment.

CONCLUSION

IR-SWIET offers better cortical lesion depiction than SWI due to CSF suppression and increased T2-weighting and provides an added tool for lesion detection in MS patients.

The invention claimed is:

1. A method of visualizing a cortical lesion in a subject using a magnetic resonance imaging (MRI) system, comprising:
   (a) acquiring signal data with the MRI system by performing a T2*-weighted sequence, wherein the sequence suppresses cerebrospinal fluid (CSF) signals; and,
   (b) from the signal data, producing one or more high resolution images, at a computer system of the MRI system, indicative of the presence of the cortical lesion, for direct visualization of the cortical lesion,
   wherein the T2*-weighted sequence comprises a T2-prepared inversion pulse (T2Prep) followed by an inversion pulse, wherein the T2Prep suppresses CSF signals.

2. A magnetic resonance imaging (MRI) system comprising:
   (a) an MRI device comprising:
      (i) a magnet system to apply a polarizing magnetic field about at least a portion of a subject arranged in the MRI system;
      (ii) a plurality of gradient coils to apply a gradient field to the polarizing magnetic field; and,
      (iii) a radiofrequency (RF) system to apply a RF excitation field to a region of interest in the subject and acquire signal data therefrom; and,
   (b) a computer system, having a processor and memory, to:
      (i) perform a T2*-weighted sequence by controlling the MRI device, wherein the sequence suppresses CSF signals;
      (ii) acquire high resolution signal data generated by the sequence; and,
      (iii) produce one or more high resolution images from the signal data for direct visualization,
   wherein the T2*-weighted sequence comprises a T2-prepared inversion pulse (T2Prep) followed by an inversion pulse, wherein the T2Prep suppresses CSF signals.

3. The method of claim 1, wherein the T2*-weighted sequence is sensitized with a diffusion gradient; and, wherein the MRI system produces diffusion-weighted images at a high isotropic resolution of about 0.6 mm or finer.

4. The method of claim 3, wherein the diffusion gradient suppresses CSF signals.

5. The method of claim 4, wherein the b-value of the diffusion gradient is 500-1200 s/mm$^2$ or higher.

6. The method of claim 5, wherein the T2*-weighted sequence is repeated, and wherein the signal data acquired from the T2*-weighted sequences are averaged to produce the one or more high resolution images.

7. The method of claim 4, wherein signal data acquired from the T2*-weighted sequence are motion corrected before producing the one or more high resolution images.

8. The method of claim 1, wherein the T2*-weighted sequence comprises a 3D-T2*-weighted multi-shot acquisition sequence, and wherein the one or more high resolution images is produced for direct visualization on at least one of: a computer screen of the MRI system; and a printout of the MRI system.

9. The method of claim 1, wherein the T2Prep comprises a $90_x$-$180_y(4)$-$90_x$ pulse.

10. The method of claim 9, wherein the duration of the T2Prep pulse is based on the calculated time at which gray matter and white matter signals are equal based on their initial magnetization values.

11. The method of claim 10, wherein the inversion time of the inversion pulse is tuned to the null point of CSF.

12. The method of claim 11, wherein the T2*-weighted sequence is repeated 2-4 times, and wherein the signal data acquired from the T2*-weighted sequences are averaged to produce the one or more high resolution images.

13. The method of claim 12, wherein the signal data acquired from the T2*-weighted sequence are motion corrected before producing the one or more high resolution images.

14. The method of claim 13, wherein the one or more high resolution images are processed from magnitude and phase images produced by the T2*-weighted sequence.

15. The method of claim 14, wherein vascular crushing is performed before the acquisition to suppress vascular signals.

16. The method of claim 15, wherein an echo train is acquired in a centric fashion.

17. The method of claim 16, further comprising performing one or more of a T1-weighted magnetization-prepared 2 rapid acquisition gradient echoes (MP2RAGE) sequence and a fluid-attenuated inversion recovery (FLAIR) sequence.

18. The method of claim 1, wherein the MRI system performs the T2*-weighted sequence at a magnetic field strength of 1.5 or 3 tesla (T).

19. The MRI system of claim 2, wherein the computer system controls the MRI device to sensitize the T2*-weighted sequence with a diffusion gradient; and, produces diffusion-weighted images at a high isotropic resolution of about 0.6 mm or finer.

20. The MRI system of claim 19, wherein the diffusion gradient suppresses CSF signals.

21. The MRI system of claim 20, wherein the b-value of the diffusion gradient is 500-1200 s/mm$^2$ or higher.

22. The MRI system of claim 21, wherein the computer system controls the MRI device to repeat the T2*-weighted sequence; and, averages the signal data acquired from the T2*-weighted sequences to produce the one or more high resolution images.

23. The MRI system of claim 19, wherein the computer system motion corrects the signal data acquired from the T2*-weighted sequence before producing the one or more high resolution images.

24. The MRI system of claim 2, wherein the T2*-weighted sequence comprises a 3D-T2*-weighted multi-shot acquisition sequence, and wherein the one or more high resolution images is produced for direct visualization on at least one of: a computer screen of the MRI system; and a printout of the MRI system.

25. The MRI system of claim 2, wherein the T2Prep comprises a $90_x$-$180_y(4)$-$90_x$ pulse.

26. The MRI system of claim 25, wherein the duration of the T2Prep pulse is based on the calculated time at which GM and WM signals are equal based on their initial magnetization values.

27. The MRI system of claim 2, wherein the computer system tunes the inversion time of the inversion pulse produced by the MRI device to the null point of CSF.

28. The MRI system of claim 2, wherein the computer system controls the MRI device to repeat the T2*-weighted sequence 2-4 times; and, averages the signal data acquired from the T2*-weighted sequences to produce the one or more high resolution images.

29. The MRI system of claim 2, wherein the computer system motion corrects the signal data acquired from the T2*-weighted sequence before producing the one or more high resolution images.

30. The MRI system of claim 2, wherein the computer system processes magnitude and phase images produced by the T2*-weighted sequence to generate the one or more high resolution images.

31. The MRI system of claim 2, wherein the computer system controls the MRI device to perform vascular crushing before the acquisition to suppress vascular signals.

32. The MRI system of claim 2, wherein the computer system acquires an echo train in a centric fashion.

33. The MRI system of claim 2, wherein the computer system controls the MRI device to further perform one or more of a MP2RAGE sequence and a FLAIR sequence; acquire one or more of MP2RAGE signal data and FLAIR signal data produced by the one or more of the MP2RAGE and FLAIR sequences; and, generate one or more MP2RAGE high-resolution images, FLAIR high-resolution images, or a combination thereof, from the one or more MP2RAGE signal data and FLAIR signal data.

34. The MRI system of claim 33, wherein the computer system controls the MRI device to perform the T2*-weighted sequence twice; and, averages the signal data acquired from the T2*-weighted sequences; and, wherein the one or more high resolution images produced from the T2*-weighted sequences are produced from the averaged signal data.

35. The MRI system of claim 34, wherein the average is a voxel-wise median or mean.

36. The MRI system of claim 2, wherein the polarizing magnetic field is 1.5 or 3 T.

* * * * *